United States Patent
Hamner et al.

(10) Patent No.: US 10,603,482 B2
(45) Date of Patent: Mar. 31, 2020

(54) SYSTEMS AND METHODS FOR PERIPHERAL NERVE STIMULATION IN THE FINGER OR HAND TO TREAT HAND TREMORS

(71) Applicant: Cala Health, Inc., Burlingame, CA (US)

(72) Inventors: Samuel Richard Hamner, San Francisco, CA (US); Kathryn H. Rosenbluth, San Francisco, CA (US); Serena HanYing Wong, Palo Alto, CA (US); Swaril Mathur, Laguna Niguel, CA (US); Paula Jean Chidester, Menlo Park, CA (US); Terence D. Sanger, Los Angeles, CA (US)

(73) Assignee: Cala Health, Inc., Burlingame, CA (US)

( * ) Notice: Subject to any disclaimer, the term of this patent is extended or adjusted under 35 U.S.C. 154(b) by 182 days.

(21) Appl. No.: 15/762,043

(22) PCT Filed: Sep. 23, 2016

(86) PCT No.: PCT/US2016/053513
§ 371 (c)(1),
(2) Date: Mar. 21, 2018

(87) PCT Pub. No.: WO2017/053847
PCT Pub. Date: Mar. 30, 2017

(65) Prior Publication Data
US 2018/0236217 A1    Aug. 23, 2018

Related U.S. Application Data

(60) Provisional application No. 62/222,210, filed on Sep. 23, 2015, provisional application No. 62/251,617, filed on Nov. 5, 2015.

(51) Int. Cl.
*A61N 1/04* (2006.01)
*A61N 1/36* (2006.01)

(52) U.S. Cl.
CPC .......... *A61N 1/0456* (2013.01); *A61N 1/048* (2013.01); *A61N 1/0484* (2013.01); *A61N 1/36003* (2013.01); *A61N 1/36031* (2017.08)

(58) Field of Classification Search
CPC ............... A61N 1/0484; A61N 1/0456; A61N 1/36031; A61N 1/36003; A61N 1/048
See application file for complete search history.

(56) References Cited

U.S. PATENT DOCUMENTS 9,877,680 B1 *   1/2018   Giuffrida ............. A61B 5/0024
2004/0127939 A1 *   7/2004   Grey ....................... A61N 1/32
606/204

* cited by examiner

*Primary Examiner* — Michael W Kahelin
(74) *Attorney, Agent, or Firm* — Knobbe, Martens, Olson & Bear LLP

(57) ABSTRACT

Systems, devices, and methods for stimulating peripheral nerves in the fingers or hand to treat tremor are described. For example, a wearable ring device for delivering electrical stimulation to sensory nerves in a patient's finger can include an annular ring having a plurality of electrodes and a detachable unit having a power source and a pulse generator.

20 Claims, 23 Drawing Sheets

HORIZONTAL CONFIGURATION
ELECTRODE STRIP DIMENSIONS

| L | 6 cm |
|---|---|
| w | 2 cm |
| h | 0.75 cm |
| S | 1 cm |
| T | 2 cm |

SYSTEMS AND METHODS FOR PERIPHERAL NERVE STIMULATION IN THE FINGER OR HAND TO TREAT HAND TREMORS

CROSS REFERENCE TO RELATED APPLICATIONS

This application is the U.S. National Stage of PCT App. No. PCT/US2016/053513 which claims priority to U.S. Provisional Application No. 62/222,210, filed Sep. 23, 2015, and U.S. Provisional Application No. 62/251,617, filed Nov. 5, 2015, each of the foregoing of which is herein incorporated by reference in their entireties.

INCORPORATION BY REFERENCE

All publications and patent applications mentioned in this specification are herein incorporated by reference to the same extent as if each individual publication or patent application was specifically and individually indicated to be incorporated by reference.

This application may be related to International Patent Application No. PCT/US2014/012388, filed Jan. 21, 2014, International Patent Application No. PCT/US2015/033809, filed Jun. 2, 2015, and International Patent Application No. PCT/US2016/037080, filed Jun. 10, 2016, each of which is herein incorporated by reference in its entirety.

Campero M, Serra J, Ochoa J L. Peripheral projections of sensory fascicles in the human superficial radial nerve. Brain 2005; 128:892-895.

Halonen J P, Jones S, Shawkat F. Contribution of cutaneous and muscle afferent fibres to cortical SEPs following median and radial nerve stimulation in man. Electroenceph Clin Neurophysiol 1988; 71:331-335.

Laroy V, Spaans F, Reulen J. The sensory innervation pattern of the fingers. J Neurol 1998; 245:294-298.

Nardone A, Schieppati M. Influences of transcutaneous electrical stimulation of cutaneous and mixed nerves on subcortical and cortical somatosensory evoked potentials. Electroenceph Clin Neurophysiol 1989; 74:24-35.

Takanashi M, Abe K, Yanagihara T, Sakoda S, Tanaka H, Hirabuki N, Nakamura H, Fujita N. A functional MRI study of somatotopic representation of somatosensory stimulation in the cerebellum. Neuroradiology 2003; 45:149-152.

Wardman D L, Gandevia S C, Colebatch J G. Cerebral, subcortical, and cerebellar activation evoked by selective stimulation of muscle and cutaneous afferents: an fMRI study. Physiol Rep, 2014; 2(4):1-16.

Wiestler T, McGonigle D J, Diedrichsen J. Integration of sensory and motor representations of single fingers in the human cerebellum. J Neurophysiol 2011; 105:3042-305.

FIELD

Embodiments of the invention relate generally to systems, devices, and methods for treating tremor using peripheral nerve stimulation, and more specifically to systems, devices, and methods for stimulating peripheral nerves in the fingers or hand to treat tremor.

BACKGROUND

Essential tremor (ET) is the most common movement disorder in the United States and currently affects an estimated 10 million individuals. Its prevalence increases with age, making it a growing concern for the U.S. aging population. ET affects 6.3% of the population over 65, but over 20% of people over the age of 95. It is characterized by 4-7 Hz oscillatory movement in the distal limbs, especially the hands. Unlike Parkinsonian tremor, which predominantly occurs during rest, essential tremor is postural (induced by holding a limb against gravity) and kinetic (present during movement).

Tremor is also a significant problem for patients with orthostatic tremor, multiple sclerosis, dystonia and Parkinson's disease. Although the underlying etiology of tremor in these conditions differs from that of ET, treatment options are similarly limited.

A number of conditions, such as tremors, can be treated through some form of transcutaneous peripheral nerve stimulation. Previous work and patent applications (e.g., PCT/US2014/012388, PCT/US2015/033809, PCT/US2016/037080) have focused on applying stimulation to the median, radial, and/or ulnar nerves on the arm or wrist. However, applying stimulation to the arm or wrist remains challenging because of natural variation in wrist diameter, nerve locations, nerve depolarization characteristics, and skin conduction. This leads to significant challenges in designing a device to comfortably, safely, and reliably stimulate the peripheral nerves across a broad population of potential users. For example, variation in the size and location of the ulnar styloid process (i.e., a bony formation on the wrist) may prevent the comfortable application of a wrist-worn stimulator that requires an electrode to conform to the wearer's skin. Additionally, as the wrist has a large range of motion with many tendons, there may be greater variability in stimulation sensation of a wrist worn stimulator due to normal hand motion.

SUMMARY OF THE DISCLOSURE

The present invention relates generally to systems, devices, and methods for treating tremor using peripheral nerve stimulation, and more specifically to systems, devices, and methods for stimulating peripheral nerves in the fingers or hand to treat tremor.

Prior neurophysiology research studies have demonstrated that electrical stimulation of the digits in the hand can activate similar pathways in the brain and spine as stimulation of individual mixed nerves at the wrist (Halonen et al., 1988; Nardone et al., 1990; Takanashi et al., 2003; Wiestler et al., 2011; Wardman et al., 2014). The sensory innervation of the hand has been mapped out in detail (Laroy et al., 1998; Campero et al., 2005), providing a rationale for selective targeting of individual nerves by applying focal cutaneous stimulation of digits.

To overcome challenges with anatomical sizing, variation in nerve location, and comfort, this application describes devices and methods for applying electrical stimulation to the nerves that innervate the hand and fingers. As shown in FIGS. 1A and 1B, the branches of the median, radial, and ulnar nerves that innervate the hand and fingers can be stimulated by a device worn on the hand or fingers and achieve tremor reduction. Further, targeting the nerves at the fingers improves stimulation specificity since nerves at the finger are predominantly sensory (i.e., afferent) while nerves at the wrist contain both sensory (i.e., afferent) and motor fibers (i.e., efferent). The electrodes are positioned to target the sensory branches of the median, radial and ulnar nerves in the hand. Specifically, these afferent nerves may carry cutaneous sensory information about the position of the fingers in time and space to the central nervous system. In addition, various pairs of nerves, such as the radial and median nerve, can be selectively stimulated by stimulating the index and middle fingers and the thumb, which also avoids stimulation of ulnar nerve. Stimulation of the little finger allow selective stimulation of the ulnar nerve, and stimulation of the ring finger allows stimulation of all three nerves. As shown in FIG. 2, this sensory information is thought to input into or be transmitted to the thalamic relay nuclei (e.g., ventral posterolateral (VPL) or ventral intermediate (VIM) nucleus) pathway, where it may intersect and disrupt or desynchronize the tremor circuit in the central nervous system.

As a proof of concept, two patients with tremor have been stimulated on their index finger to assess the effect of electrical stimulation of the finger on reduction of hand tremors. Patient 01 was a 69 year old male. The top and middle segments of the index finger were stimulated on the palmar side of the finger with a 1 cm×2 cm electrode pair, as shown in FIG. 3A. Patient 01 received constant stimulation at 150 Hz for 30 minutes. Spirals drawn pre-stimulation and post-stimulation show a noticeable reduction in hand tremor, as shown in FIG. 3B. Patient 02 was a 61 year old female tested on Sep. 11, 2015. The patient was stimulated on the distal segment of the index finger with two 1 cm×2 cm electrode pairs, as shown in FIG. 4A (i.e., an electrode pair on the palmar side and an electrode pair on the dorsal side). The stimulation alternated a 150 Hz biphasic waveform between the electrode pairs at a frequency that matched the patient's measured tremor frequency (e.g., between 4-12 Hz). Spirals drawn pre-stimulation and post-stimulation show a noticeable reduction in hand tremor as shown in FIG. 4B. Both subjects were consented under an IRB approved protocol.

Additionally, social stigma and embarrassment greatly affect the quality of life of people with ET and other types of hand tremor. A hand-worn device or ring can have a form that is more discreet than an arm or wrist-worn device. This is relevant during social and other public situations when it is desired to keep the tremor reduction therapy discreet. Additionally, compared to the arm or wrist, less power is required to stimulate the branches of the median, radial, and ulnar nerves in the hand and fingers. This would allow for a smaller power source and stimulator.

Additionally, a peripheral nerve stimulator worn on the finger, such as a ring, provides better contact with the wearer's skin. This is due in part to the tissue composition in the finger, which includes malleable fatty tissue, and reduced patient to patient size variation in the finger as compared to other body parts, such as the wrist. Movement of the finger is less likely to move the device relative to the locations of the median, radial, and ulnar nerves. This allows a hand or finger-worn device to maintain strong contact with the skin throughout the range of normal motion. This contact enables the use of dry- or wetted-electrodes instead of sticky gels and adhesives.

Additionally, there are advantages to measuring upper extremity tremor motion at the hand and/or fingers, as opposed to the arm and/or wrist. While it is possible to generate data and measure tremor motion at the arm and/or wrist, it is more accurate to do so at the hand and/or fingers. Tremor at the hand and/or fingers is a better representation of the functional impact that tremor has on a patient's ability to perform activities of daily living.

In some embodiments, a wearable ring device for treating hand tremors by electrically stimulating one or more sensory nerves on a finger of a patient's hand is provided. The device includes an annular member defining an aperture that is sized to receive a finger of the patient; a first electrode, a second electrode, and a third electrode housed on an inside surface of the annular member and configured to be in contact with the patient's skin when worn on the finger; and a stimulation unit that is configured to connect to the annular member, wherein when the unit is connected to the annular member the unit is in electrical communication to the first electrode, the second electrode, and the third electrode, wherein the unit houses a power source and a pulse generator configured to deliver pulsed electrical stimulation to the one or more sensory nerves in the finger.

In some embodiments, when worn the first electrode is configured to be positioned on the dorsal side of the finger, the second electrode is configured to be positioned on the palmar side of the finger, and the third electrode is configured to be positioned between the first and second electrodes.

In some embodiments, the third electrode is a common ground electrode.

In some embodiments, the finger is the index finger, middle finger, or the ringer finger.

In some embodiments, the device further includes a fourth electrode housed on the inside surface of the annular member.

In some embodiments, the power source is a capacitor.

In some embodiments, the power source is a rechargeable battery.

In some embodiments, the stimulation unit is detachable.

In some embodiments, the third electrode is configured to be positioned approximately equidistant between the first and second electrodes when the device is worn.

In some embodiments, the first, second, and third electrodes comprise a dry conductive polymer or rubber with a textured surface configured to capture moisture from the skin, air, or other external sources.

In some embodiments, the first, second, and third electrodes comprise a wicking conductive fabric configured to capture moisture from the skin, air, or other external sources.

In some embodiments, the device further includes a wireless transceiver electrically connected to the pulse generator and configured to communicate with at least one external electronic device.

In some embodiments, the annular member comprises a flexible housing material, and the first, second, and third electrodes are electrically connected with flexible electronic circuitry that is configured to conform to a predetermined range of finger diameters and configured to accommodate variation in finger diameter over time.

In some embodiments, the annular member comprises one or more motion sensors, and wherein the pulse generator is configured to modulate the pulsed electrical stimulation based on measurements of tremor motion and activity from the one or more motion sensors, wherein the one or more motion sensors are selected from the group consisting of an inertial measurement unit, an accelerometer, a gyroscope, and a magnetometer.

In some embodiments, the one or more motion sensors in the annular member along with a processor located in the stimulation unit or at least one external device are configured to measure and detect one or more predetermined motions and to modulate the pulsed electrical stimulation based on the measurement and detection of the one or more predetermined motions.

In some embodiments, one or more predetermined motions is selected from the group consisting of knocking the hand of the patient on an object a predetermined number of times, raising the arm up, waving the hand, opening and closing the hand, tapping the finger on a table a predetermined number of times, snapping the fingers, clapping of hands, and pointing.

In some embodiments, the inside surface of the annular member is free from gels and adhesives.

In some embodiments, the device further includes a second annular member defining an aperture that is sized to receive the first finger of the patient, wherein the second annular member comprises one or more motion sensors configured to measure motion of the patient's hand.

In some embodiments, the second annular member is configured to communicate with the stimulation unit and/or the at least one external device.

In some embodiments, the second annular member is configured to detachably connect to the stimulation unit.

In some embodiments, the second annular member comprises a wireless transceiver.

In some embodiments, when worn the first electrode is configured to be positioned on the dorsal side of the first finger, the second electrode is configured to be positioned on the palmar side of the first finger, and the third electrode is a circumferential electrode configured to be positioned circumferentially on the inside surface of the annular member and proximal of first and second electrodes.

In some embodiments, a wearable ring device for treating hand tremors by electrically stimulating one or more sensory nerves on one or more fingers of a patient's hand is provided. The device includes a first annular member defining an aperture that is sized to receive a first finger of the patient, wherein the first finger is an index, middle, or ring finger; a second annular member defining an aperture that is sized to receive a second finger of the patient; a first electrode and a second electrode disposed on an inside surface of the first annular member and configured to be in contact with the patient's skin when worn on the first finger; a third electrode and a fourth electrode disposed on an inside surface of the annular member and configured to be in contact with the patient's skin when worn on the second finger; and a unit housing a power source and a pulse generator configured to deliver pulsed electrical stimulation to the one or more sensory nerves through the first electrode and the second electrode, and the third electrode and the fourth electrode.

In some embodiments, a method of reducing tremor in a patient's hand is provided. The method includes measuring motion in the patient's hand with a sensor worn on one of the patient's fingers; determining one or more characteristics of the tremor based on a signal generated by the motion sensor; and stimulating one or more sensory nerves in a first finger of the patient according to a set of stimulation parameters using a wearable stimulator, wherein the set of stimulation parameters is based in part on the one or more of the determined tremor characteristics, wherein the one or more sensory nerves is selected from the group consisting of the medial nerve, the radial nerve, and the ulnar nerve.

In some embodiments, the one or more characteristics of the tremor is selected from the group consisting of the tremor frequency, tremor amplitude, and tremor phase.

In some embodiments, the step of stimulating one or more sensory nerves comprises stimulating two sensory nerves.

In some embodiments, the method further includes isolating tremor based motion from non-tremor based motion in the measured motion.

In some embodiments, a system for treating hand tremors by electrically stimulating one or more sensory nerves on a finger of a patient's hand is provided. The system includes a ring device that includes an annular member defining an aperture that is sized to receive a first finger of the patient, wherein the first finger is an index or a middle finger; and a first electrode, a second electrode, and a third common ground electrode housed on an inside surface of the annular member and configured to be in contact with the patient's skin when worn on the first finger. The system further includes a wrist unit in electrical communication with the ring device that is configured to be worn around the patient's wrist, wherein the wrist unit houses a processor, a power source, and a pulse generator configured to deliver pulsed electrical stimulation to the one or more sensory nerves in the first finger through the ring device.

In some embodiments, a system for treating hand tremors by electrically stimulating one or more sensory nerves on a finger of a patient's hand is provided. The system includes a ring device that includes an annular member defining an aperture that is sized to receive a first finger of the patient, wherein the first finger is an index or a middle finger; and a first electrode, a second electrode, and a third common ground electrode housed on an inside surface of the annular member and configured to be in contact with the patient's skin when worn on the first finger. The system further includes a mobile phone comprising a processor and a battery; and an adapter in electrical communication with both the ring device and the mobile phone, wherein the adapter comprises a pulse generator configured to deliver pulsed electrical stimulation to the one or more sensory nerves in the first finger through the ring device, wherein the mobile phone is configured to control the pulse generator.

The devices and methods of this disclosure each have several innovative aspects, no single one of which is solely responsible for the desirable attributes disclosed herein. The present application discloses devices and methods to reduce tremor in an individual. In some embodiments, a device is provided. The device can include a housing and one or more affectors, power sources, or controls. In some embodiments, the device additionally includes one or more sensors. Further aspects and embodiments of the present invention are set forth herein.

These and other aspects and embodiments of the invention are described in greater detail below, with reference to the drawing figures.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Our invention is a device and system to measure and collect motion data, analyze said data, as to interpret how these measures may influence motion disorders, and stimulate individual peripheral nerve targets to reduce tremor. The purpose of the data analysis is to see how the measured data may influence motion disorders. The applied stimulation may or may not be modified based on the measured data.

Figure 1A:
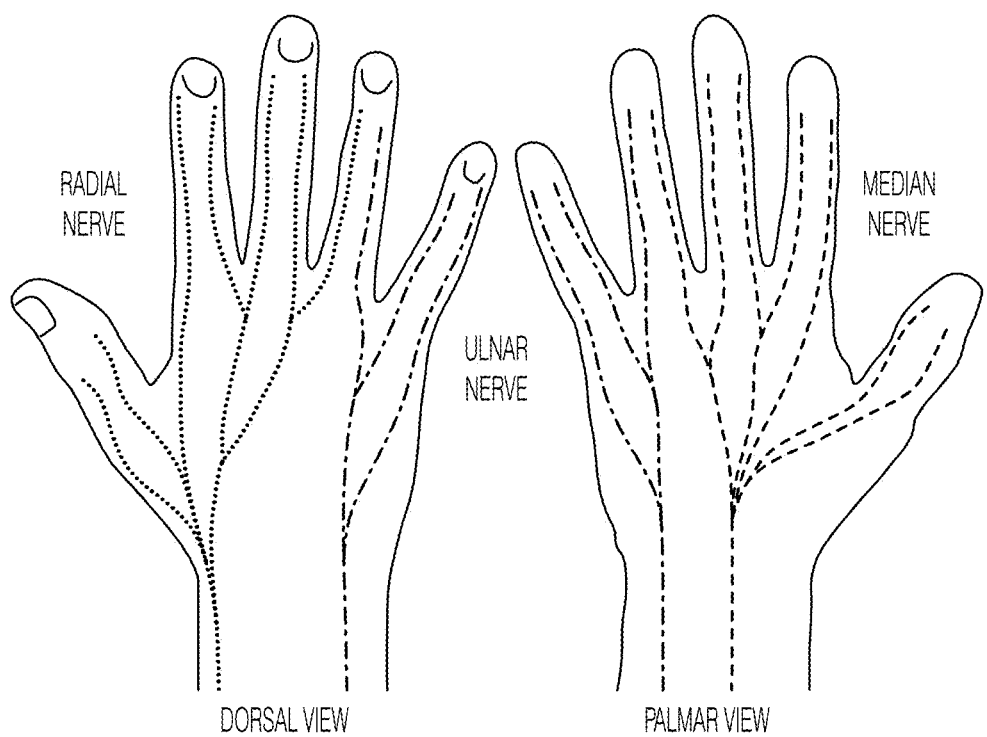
FIG. 1A illustrates a diagram of nerves and nerve distribution in the hand and fingers. Radial nerve is dotted, ulnar nerve is dash-dot, and median nerve is dashed.
Figure 1B:
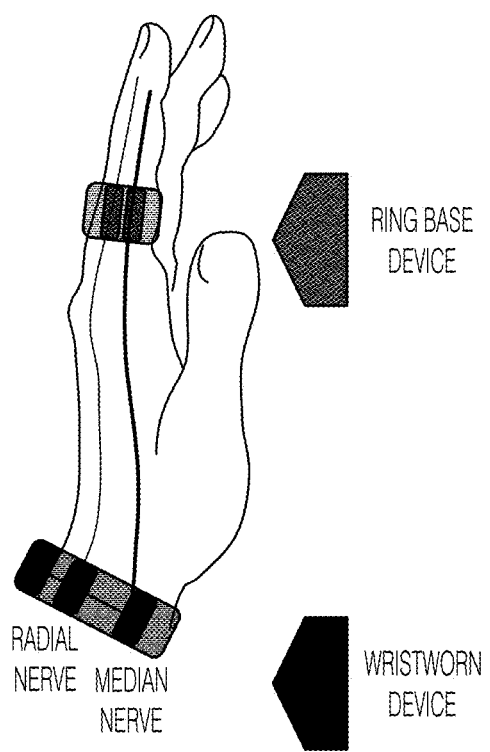
FIG. 1B illustrates a diagram of the radial and median nerve branches from the wrist to the finger, illustrating how a ring-based device could stimulate the same pathways as a wrist worn device.
Figure 2:
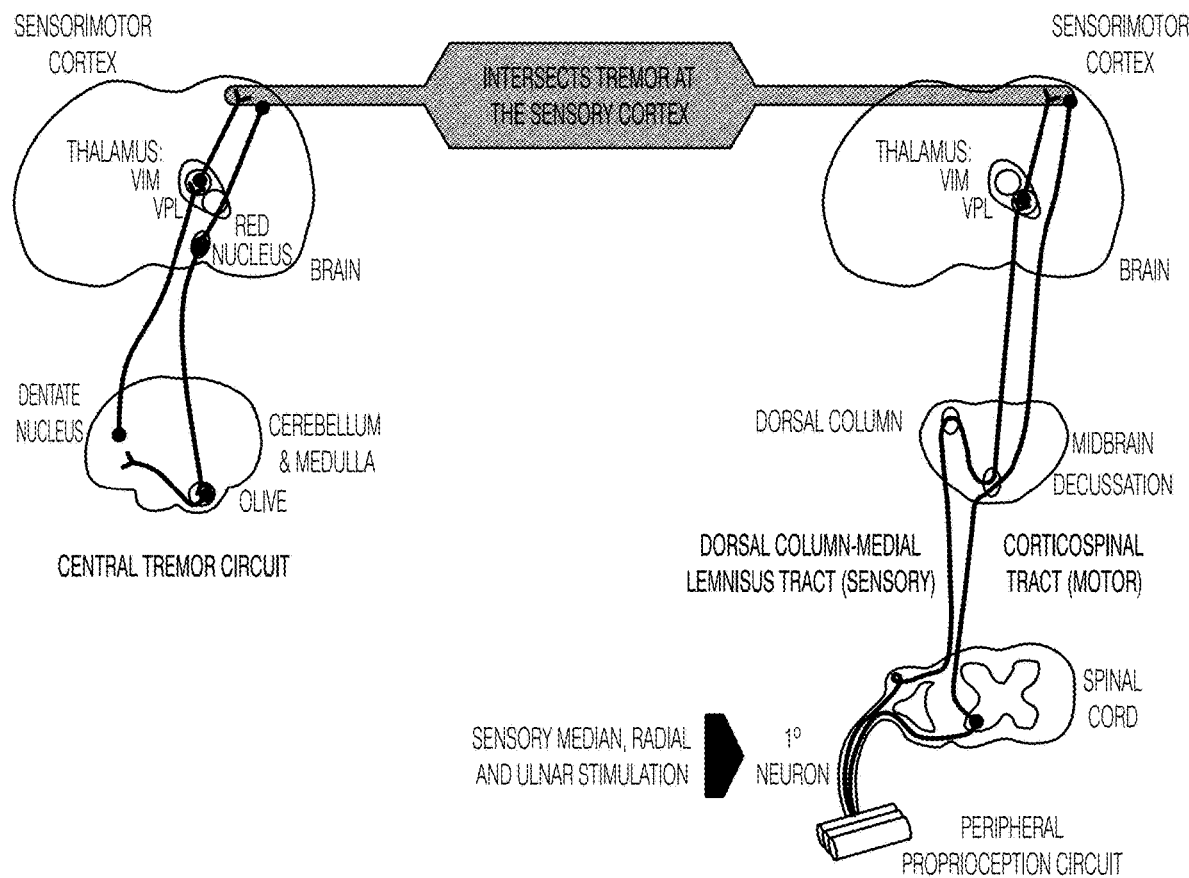
FIG. 2 illustrates how sensory stimulation from a peripheral nerve stimulation device intersects the tremor circuit in the central nervous system.
Figure 3A:
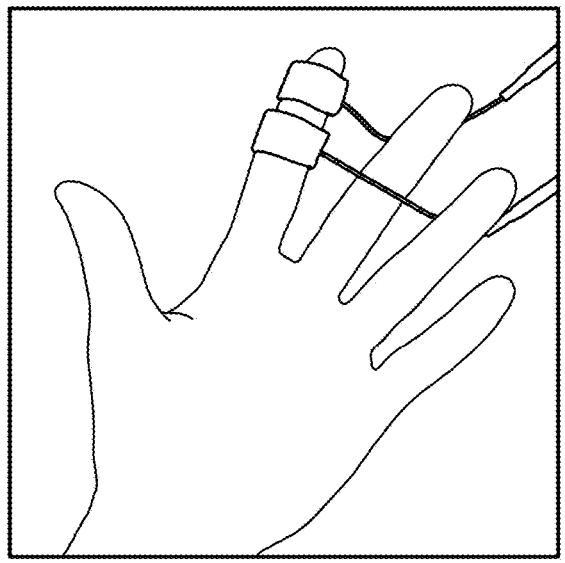
FIG. 3A illustrates an embodiment of a finger of a first patient being stimulated on the top and middle segments on the palmar side of the index finger with 1 cm×2 cm electrodes.
Figure 3B:
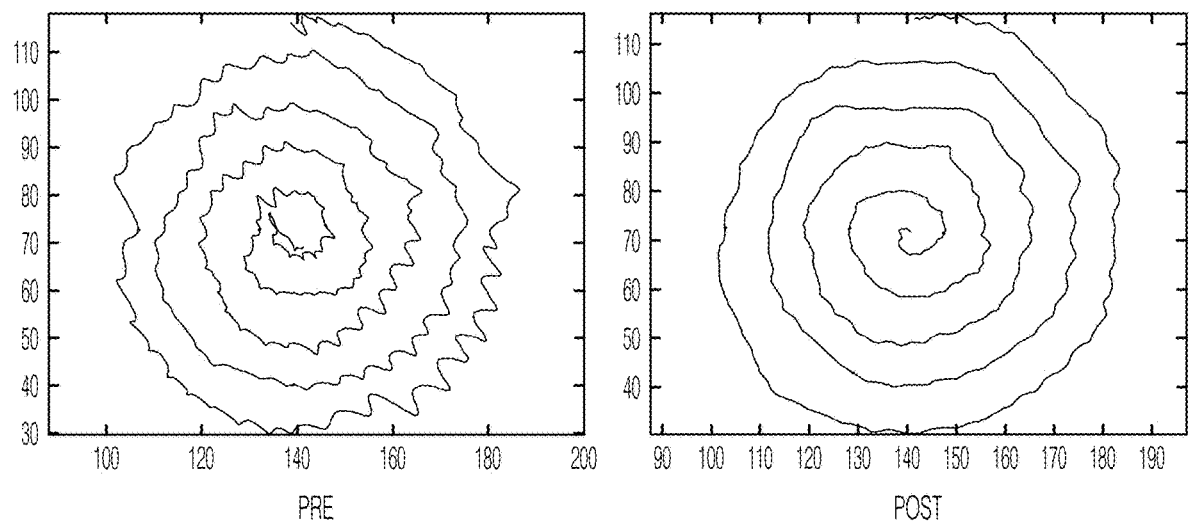
FIG. 3B illustrates spirals drawn by the first patient in FIG. 3A pre-stimulation and post-stimulation. Stimulation was constant 150 Hz bi-phasic waveform from an LGTech Elite device for 30 minutes.
Figure 4A:
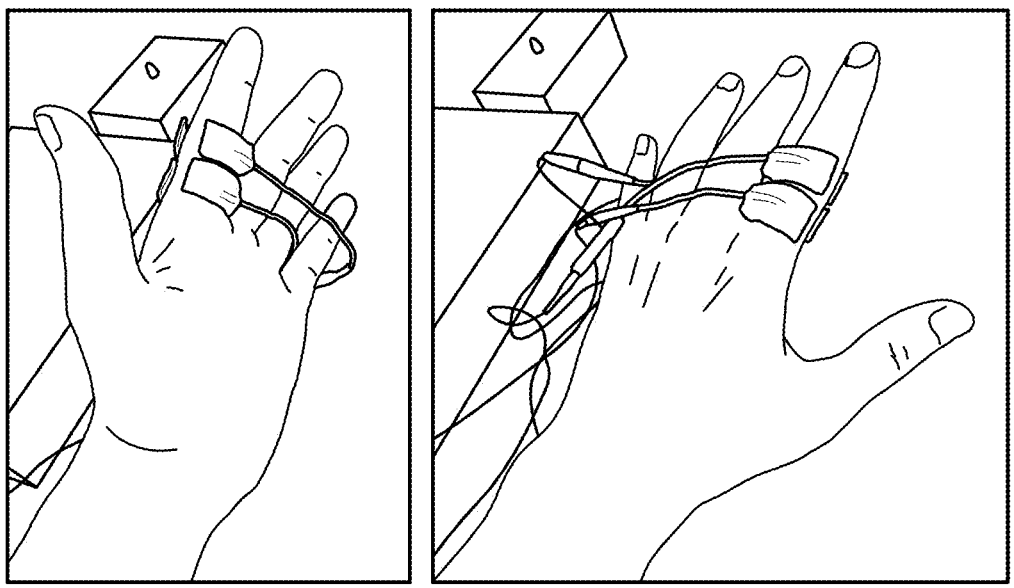
FIG. 4A illustrates an embodiment of a finger of a second patient being stimulated on the distal segment of the index finger with two 1 cm×2 cm electrode pairs, one on the palmar side and one on the dorsal side. Stimulation lasted 30 minutes and was a 150 Hz bi-phasic waveform that alternated between the electrode pairs at a frequency that matched the patient's measured tremor frequency.
Figure 4B:
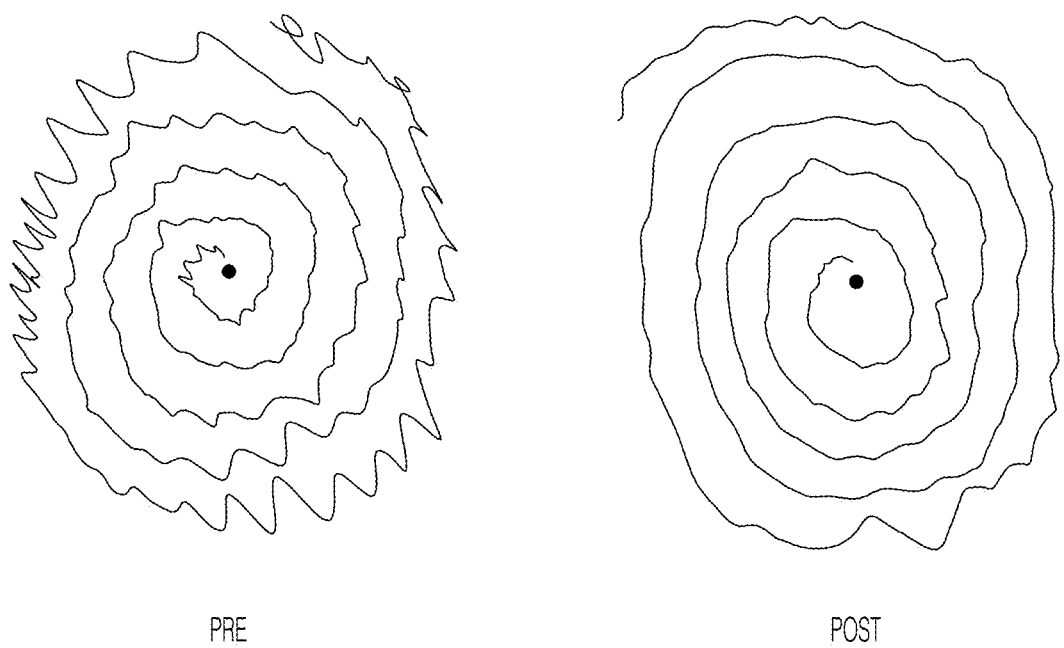
FIG. 4B illustrates spirals drawn by the second patient pre-stimulation and post-stimulation.
Figure 5A:
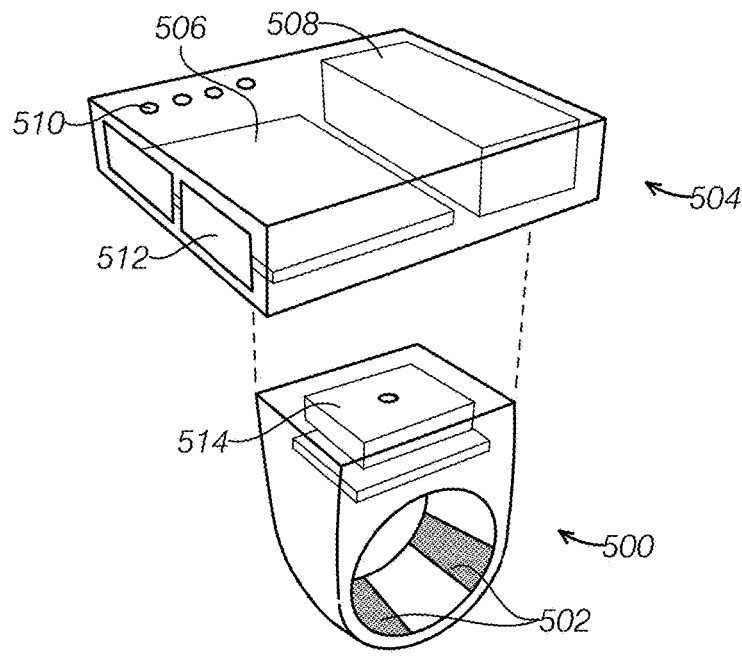
FIG. 5A illustrates an embodiment of a ring worn peripheral nerve stimulator with a RING unit to apply stimulation to the skin through electrode, which may also monitor tremor motion; and a stimulation unit that may contain an electrical stimulation signal generator, power source, and a microprocessor to control the stimulation.
Figure 5B:
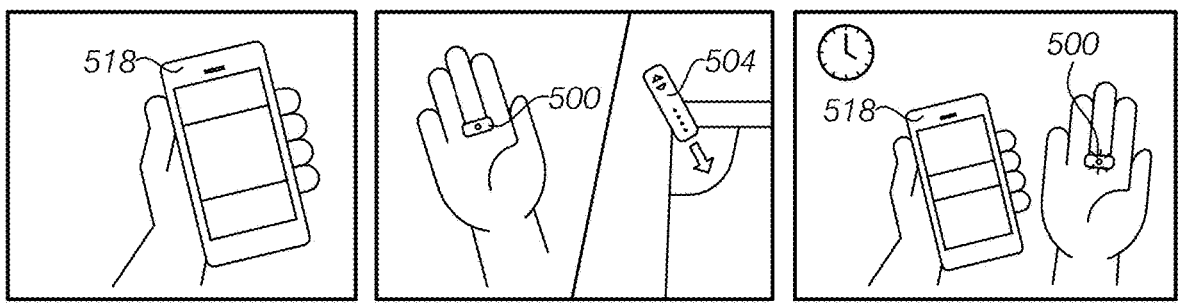
FIG. 5B illustrates how the ring and stimulation unit can be charged daily with a charging station and communicate with an external computing device, such as a smartphone or tablet, to store and analyze measured data, including stimulation parameters, and provide notifications to the ring wearer.

As shown in FIGS. 5A and 5B, one embodiment is a two-part system that includes 1) a ring-like unit 500 worn on the finger that contains electrodes 502 to transcutaneously apply electrical stimulation to the branches of the median, radial, and/or ulnar nerves in the finger, and 2) a detachable stimulation power unit 504 that may contain an electrical stimulation signal generator 506, power source 508, and/or a microprocessor to control the stimulation. The detachable stimulation power unit 504 can also have a user interface that can include a display, such as LEDs 510, and buttons 512 for entering inputs and adjusting stimulation parameters, such as amplitude. The stimulation power unit can connect directly through complementary contacts 514 on the ring-like unit 500 and/or a complementary receptacle on the stimulation power unit and/or wirelessly with the ring-like unit 500. FIG. 5B illustrates how the ring 500 and stimulation unit 504 can be charged daily with a charging station 516 and communicate wirelessly with an external computing device 518, such as a smartphone or tablet, to store and analyze measured data, including stimulation parameters, and provide notifications to the ring wearer.

Figure 7A:
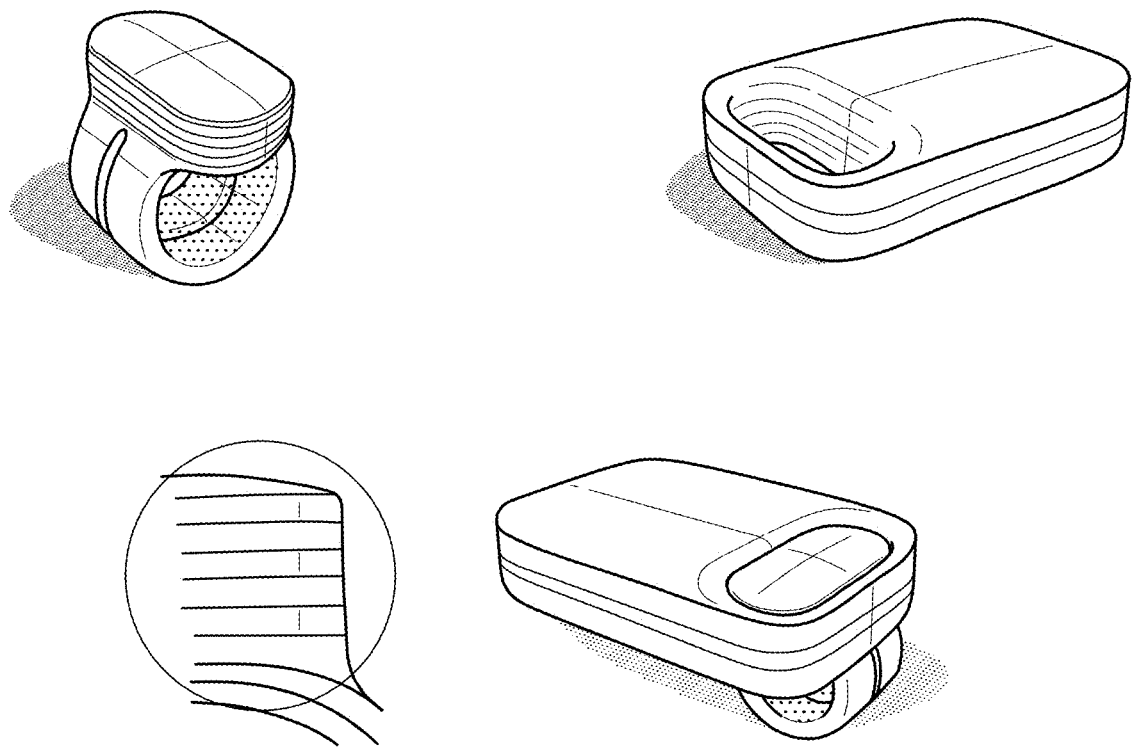
FIGS. 7A-7D illustrate additional embodiments of a ring unit and a stimulation unit.
Figure 7B:
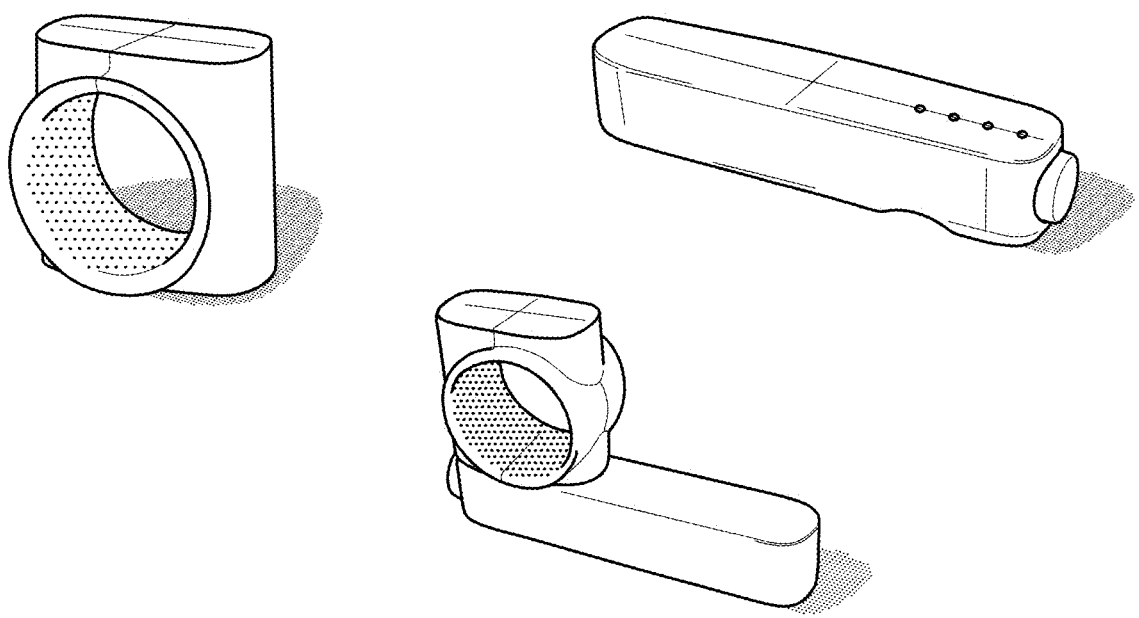
Figure 7C:
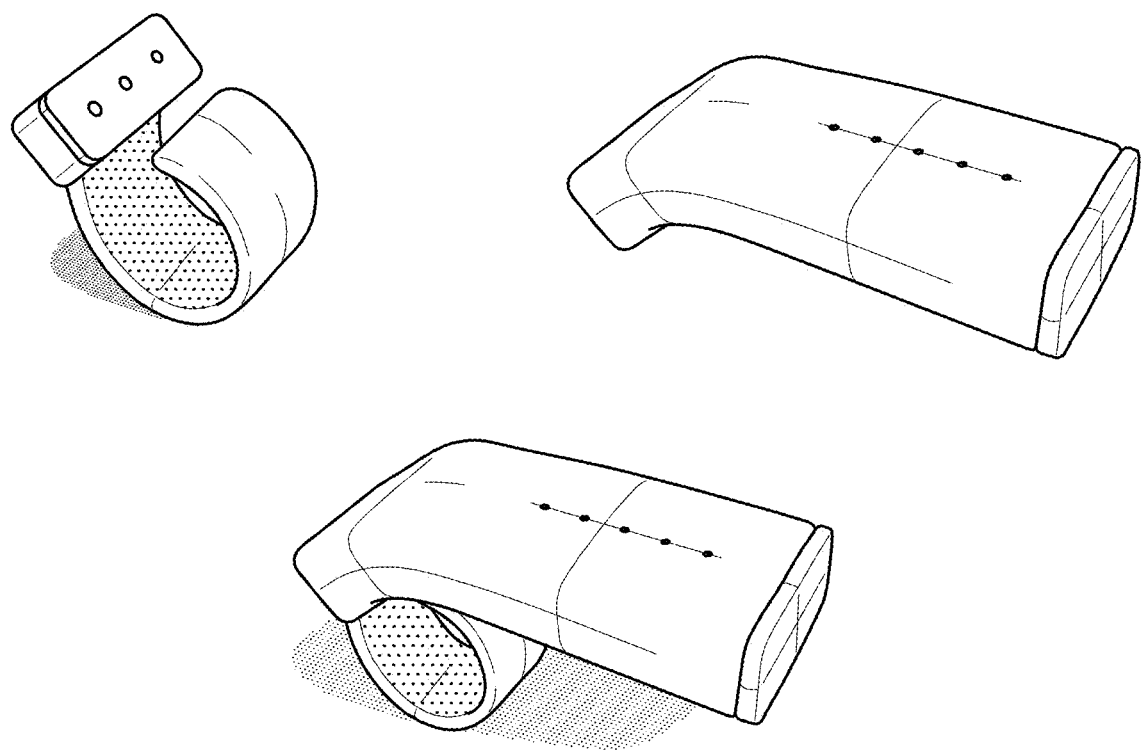
Figure 7D:
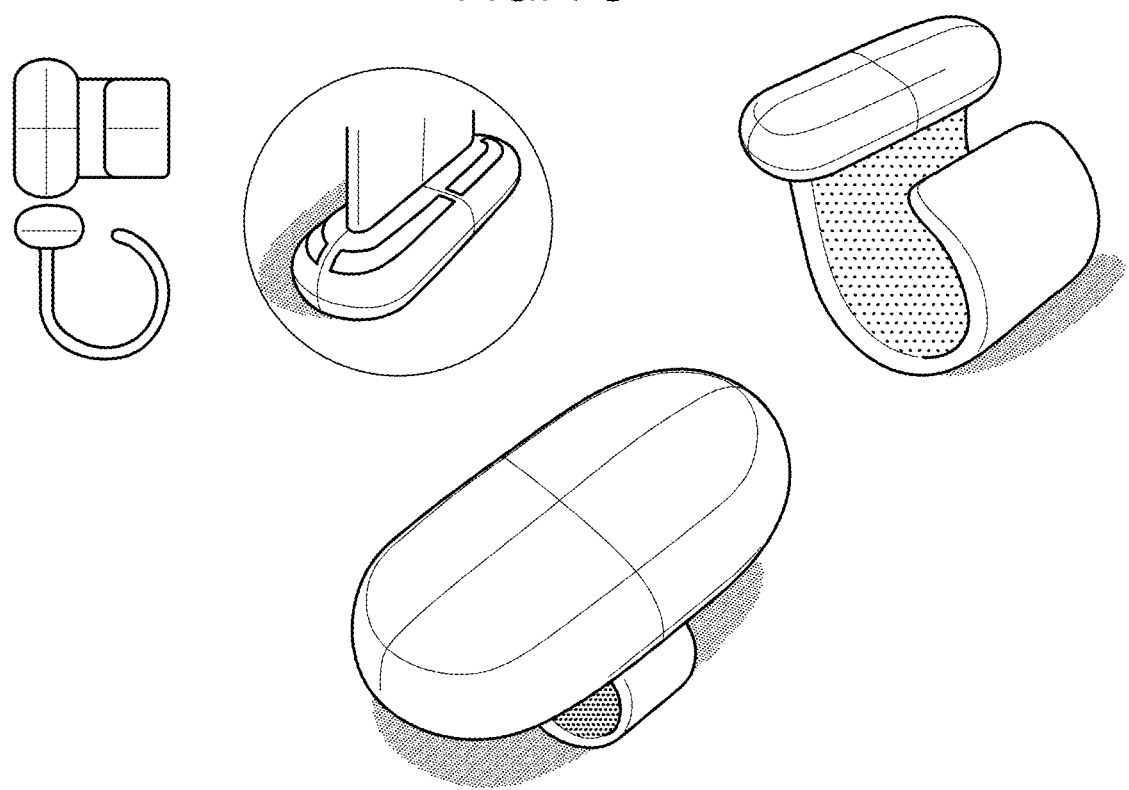
Figure 8A:
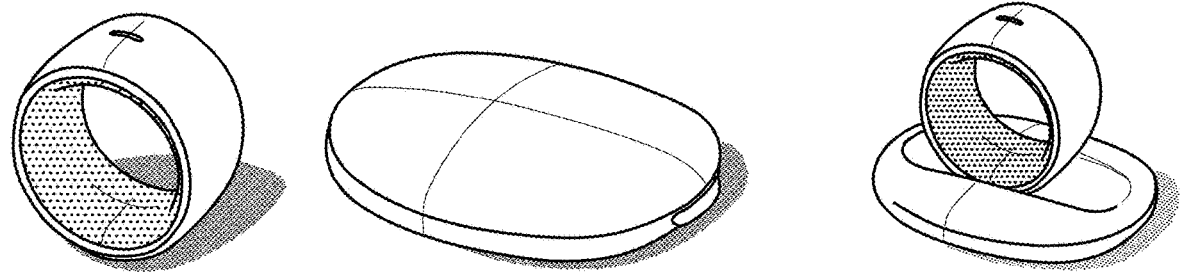
FIGS. 8A-8C illustrate additional embodiments of a ring unit and a stimulation unit.
Figure 8B:
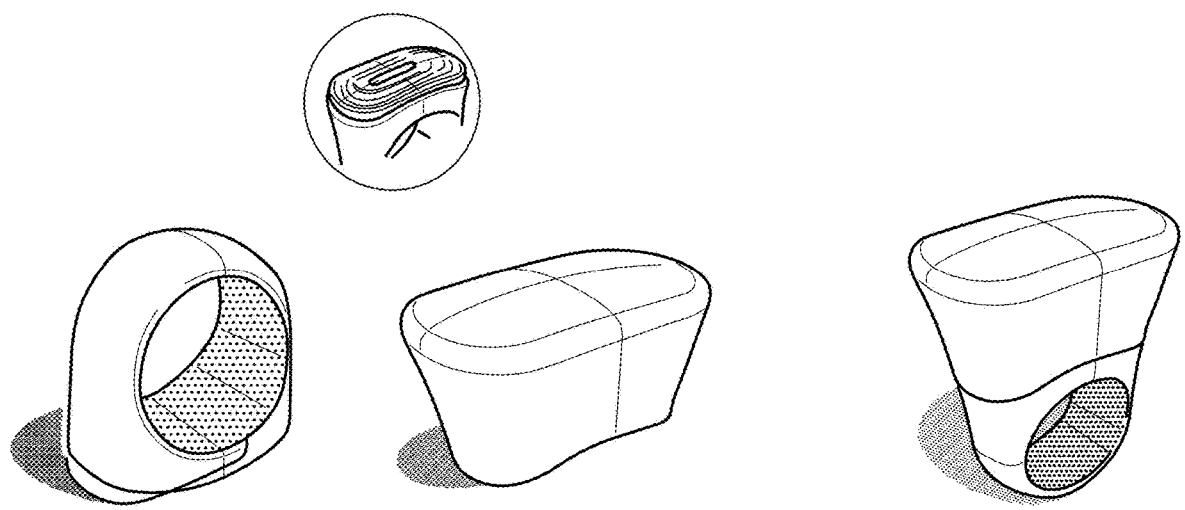
Figure 8C:
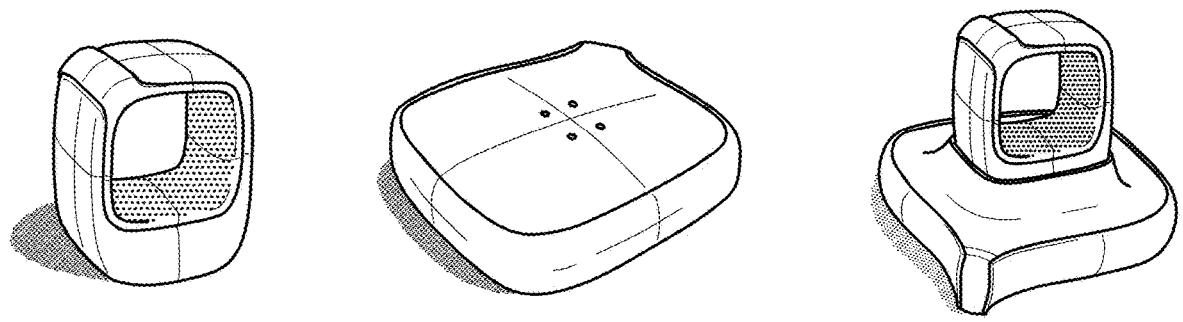

FIGS. 6A-D, FIGS. 7A-D, and FIGS. 8A-C show eleven variations of an embodiment of a two-part system that includes a ring-like unit and a stimulator unit. FIG. 7A shows a ring unit that has electrical contacts between the ring unit and stimulator that allow for two separate circumferential electrodes. FIGS. 7C-D show a ring-like unit where the mass of the ring rests at the crevice between two fingers and has an open band that is flexible to allow for variation in finger size.

In the above embodiment, the ring-like unit may contain sensors to measure tremor motion and activity using an inertial measurement unit (IMU), accelerometer, gyroscope, and/or magnetometer.

Figure 9A:
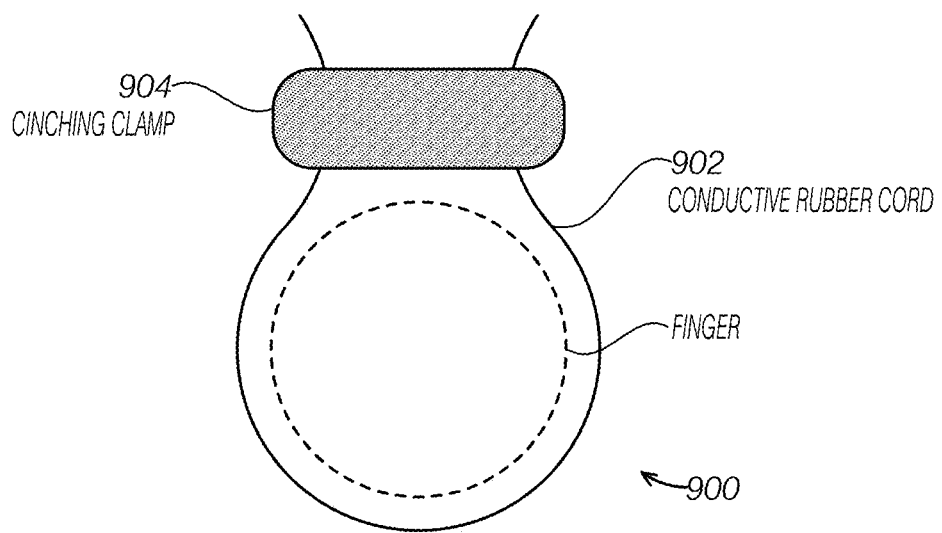
FIG. 9A illustrates an embodiment of a ring-like unit formed from a conductive rubber cord that can be cinched around a finger.
Figure 9B:
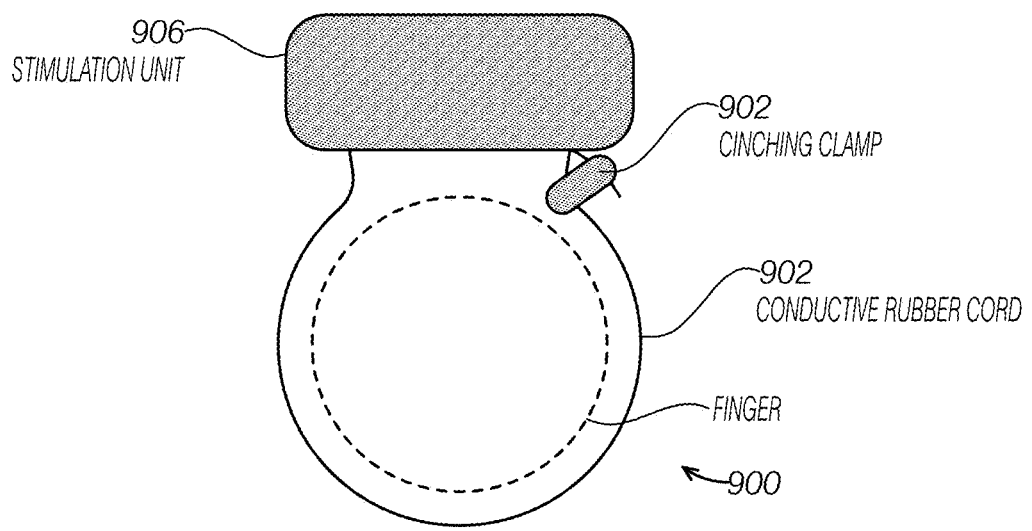
FIG. 9B illustrates the embodiment of the ring-like unit shown in FIG. 9A with a stimulation unit attached.

In any of the above embodiments, as shown in FIGS. 9A and 9B, the ring-like unit 900 may be a conductive rubber cord 902 or wire that is cinched, using a cinching claim 904 for example, to fit snuggly around the finger. The cinching rubber cord 902 may also attach a stimulation unit 906 that contain an electrical stimulation signal generator, power source, and/or a microprocessor to control the stimulation.

Figure 10:
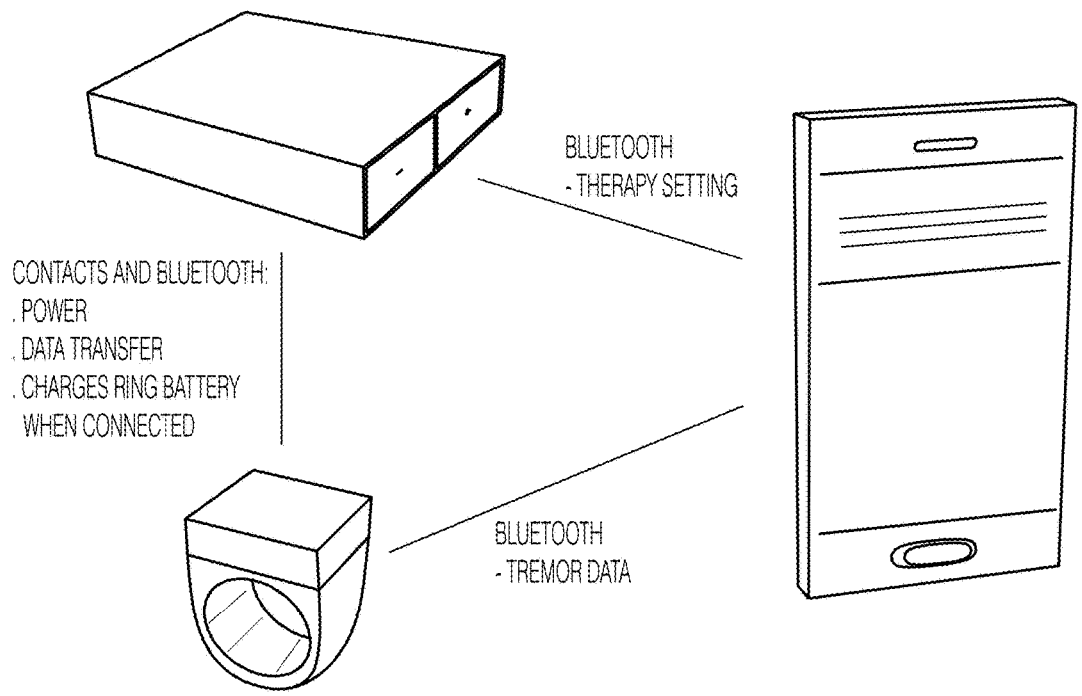
FIG. 10 illustrates an embodiment of the ring unit and the stimulation unit communicating with an external computing device, such as a smart phone and tablet, using wireless communication, such as low-energy Bluetooth.

In an extension of the above embodiment, as shown in FIG. 10, the ring unit 1000 and the stimulation unit 1002 may communicate with an external computing device 1004, such as a smart phone and tablet, using wireless communication, such as low-energy Bluetooth. The communication may also be tethered with a wired connection. Communication may be real time, at set intervals (e.g., hourly, daily, weekly), and/or when the devices are within range of each other.

Figure 11:
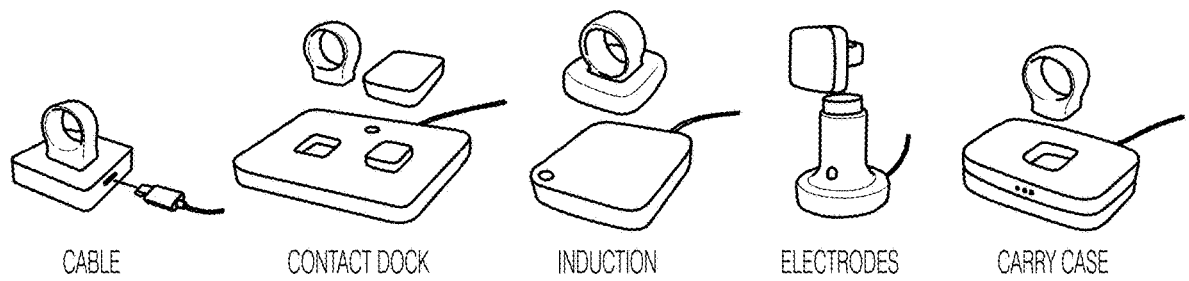
FIG. 11 illustrates embodiments for charging the ring and/or stimulation units when not being worn.

In the above embodiments, the ring unit 1000 and/or stimulation unit 1002 can be charged directly with a cable (e.g., micro USB), a contact dock 1006 with direct connection to the power source, inductive charging, direct contact with the stimulation electrodes (i.e., electrodes contact the charging station, which does not require a separate charging connection), and/or a separate carrying case, as shown in FIG. 11, that combines the above concepts on charging and data transfer.

Figure 12:
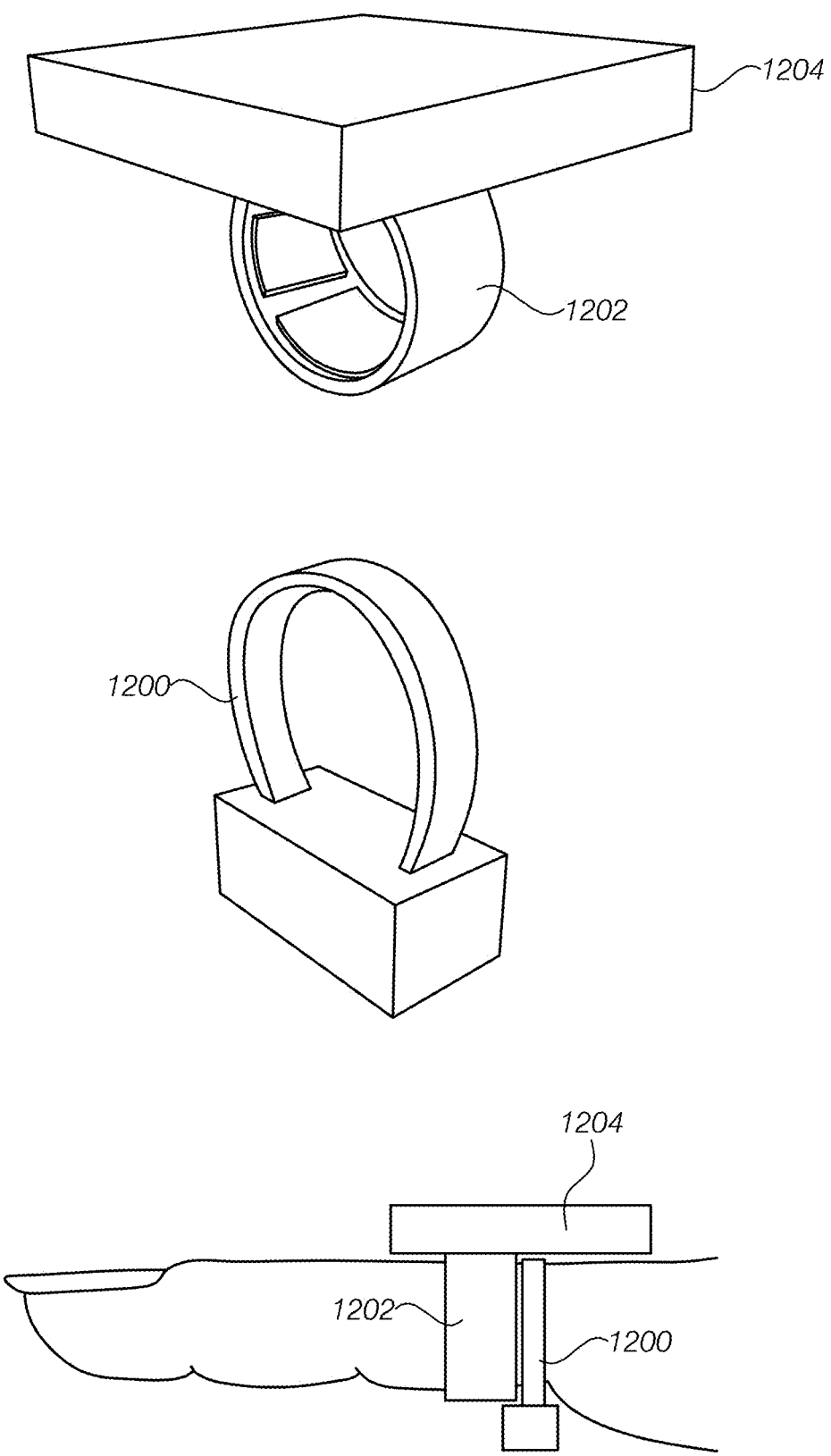
FIG. 12 illustrates an embodiment of a thin ring worn motion monitor and a separate ring worn stimulation unit that may contain an electrical stimulation signal generator, power source, and a microprocessor to control the stimulation.

Another embodiment as shown in FIG. 12 is a two-part system that includes 1) a ring-like unit 1200 worn on the finger that contains sensors to measure tremor motion and activity using an inertial measurement unit (IMU), accelerometer, gyroscope, and/or magnetometer, and 2) a second ring-like unit 1202 that contains electrodes and applies transcutaneous electrical stimulation to the branches of the median, radial, and/or ulnar nerves in the finger, an electrical stimulation signal generator, a power source, and a microprocessor to control the stimulation. The stimulation unit 1204, which is attached to the second ring unit 1202 may also be permanently affixed to the ring unit 1200 that measures motion or may be detachable from one or both ring units.

Figure 13:
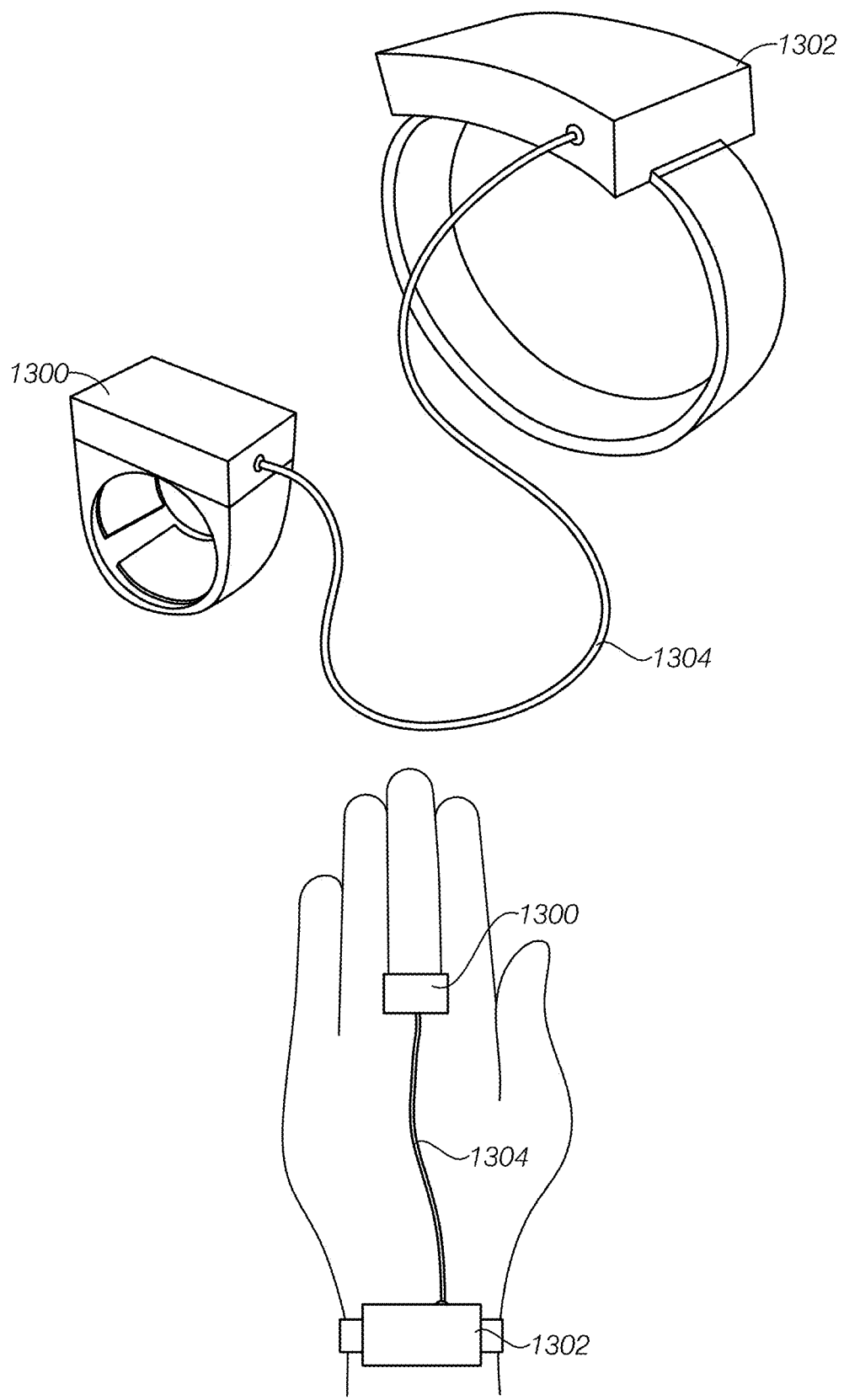
FIG. 13 illustrates an embodiment of a ring worn peripheral nerve stimulator with a ring to apply stimulation and monitor tremor motion; and a wrist worn stimulation unit that may contain an electrical stimulation signal generator, power source, and a microprocessor to control the stimulation. The wrist-worn stimulation unit is tethered by wire to the ring.

Another embodiment as shown in FIG. 13 is a two-part system that includes 1) a ring-like unit 1300 worn on the finger that contains electrodes to transcutaneously apply electrical stimulation to the branches of the median, radial, and/or ulnar nerves in the finger, and 2) a wrist-worn stimulation power unit 1302 that may contain an electrical stimulation signal generator, power source, and a microprocessor to control the stimulation. This wrist-worn power unit 1302 is tethered by wire 1304 to the ring-like unit 1300.

Figure 14:
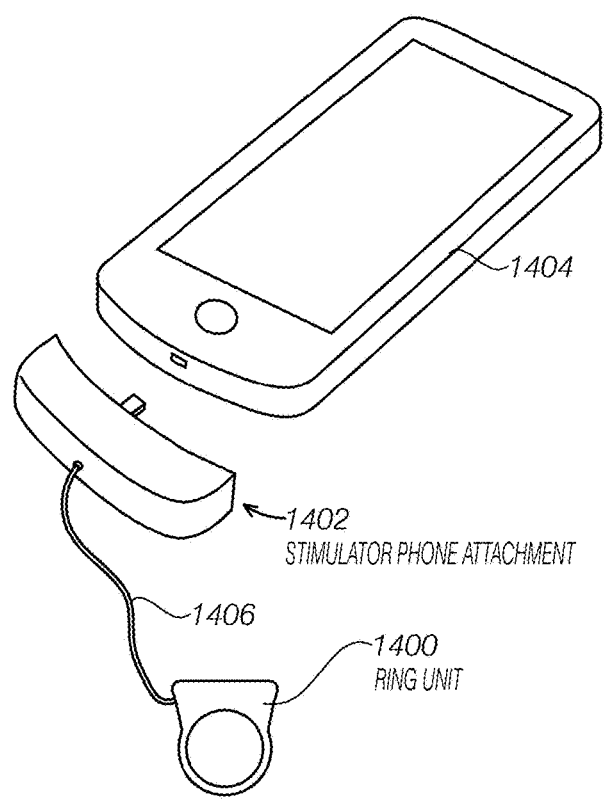
FIG. 14 illustrates an embodiment of a ring worn peripheral nerve stimulator that is connected to a smartphone or tablet through an attachment device. The ring could have minimal electronics to provide stimulation to the finger and the phone/attachment could house an electrical stimulation signal generator, power source, and a microprocessor to control the stimulation.

In another related embodiment as shown in FIG. 14, the ring unit 1400 could be attached to a non-wrist-worn (or worn device) device. Such a device could be an electronics unit 1402, such as a ring unit-phone adapter, that is connected to a mobile phone 1404 (e.g., different credit card readers). The advantage of the direct attachment to the phone is that additional electronics could be integrated into a phone case and power could be either be drawn from a separate battery hidden in the case or the phone itself. The ring unit 1400 can be tethered to the adapter through a wire 1406 which can transmit data and power from the phone to the ring unit. Additionally, this would allow easy access to the functionality of the phone, especially for services like per-treatment billing. While a phone may seem bulky, holding a phone during treatment could seem relatively normal and socially acceptable.

Figure 15:
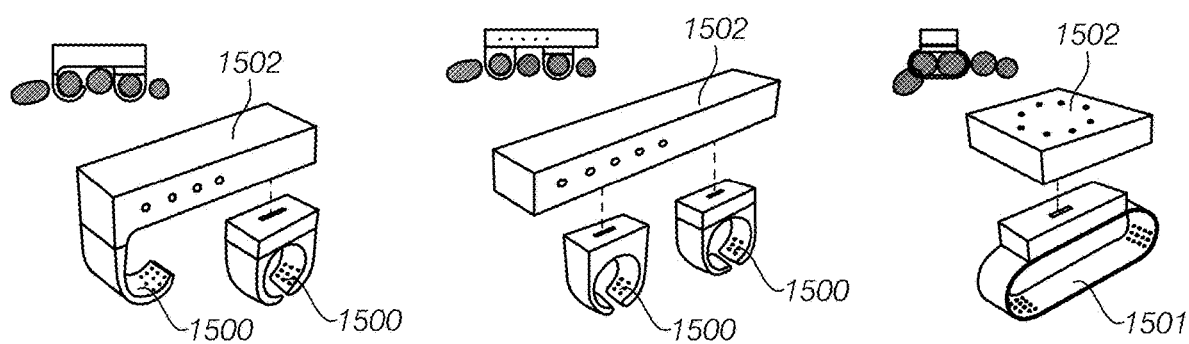
FIG. 15 illustrates an embodiment of a ring worn peripheral nerve stimulator and a stimulation unit that has multiple rings or a band that wraps the fingers to stimulate multiple fingers simultaneously.

In another embodiment as shown in FIG. 15, there could be two or three ring-like units 1500 connected with a stimulation unit 1502 to provide electrical stimulation to multiple fingers simultaneously. The ring-like unit 1501 could also be a band that wraps around multiple fingers. These ring-like units may contain electrodes to transcutaneously apply electrical stimulation to the branches of the median, radial, and/or ulnar nerves in the fingers. The stimulation unit may contain an electrical stimulation signal generator, power source, and a microprocessor to control the stimulation.

In another embodiment, the ring-like unit is a stand-alone device that has a motion monitor, electrodes, electrical stimulation signal generator, power source, and microprocessor to control the stimulation. The ring-like unit may provide transcutaneous stimulation to the branches of the median, radial, and/or ulnar nerves in the finger.

Figure 16A:
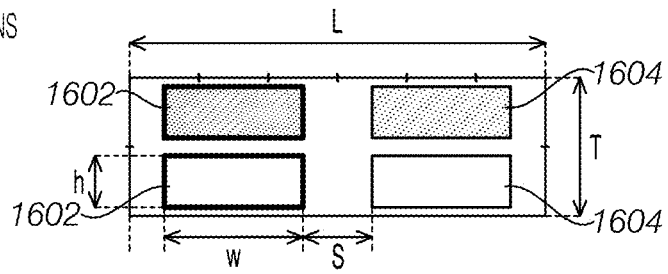
FIG. 16A illustrates an embodiment of a horizontal electrode configuration housed in a ring-like unit that provides electrical stimulation transcutaneously to nerves in the finger. This illustration is of an index finger with an electrode pair on the dorsal side to stimulate the radial nerve, and an electrode pair on the palmar side to stimulate the median nerve.
Figure 16A:
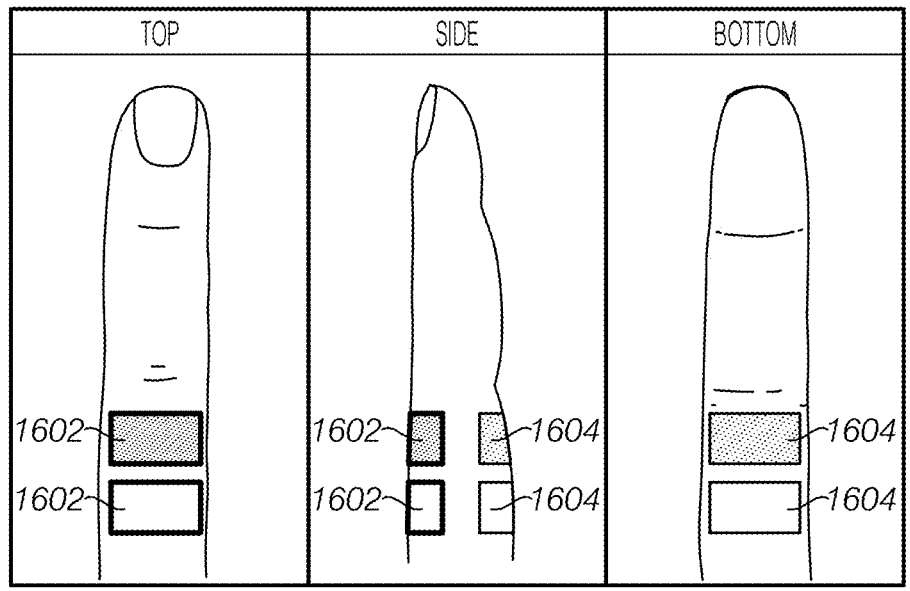
Figure 16B:
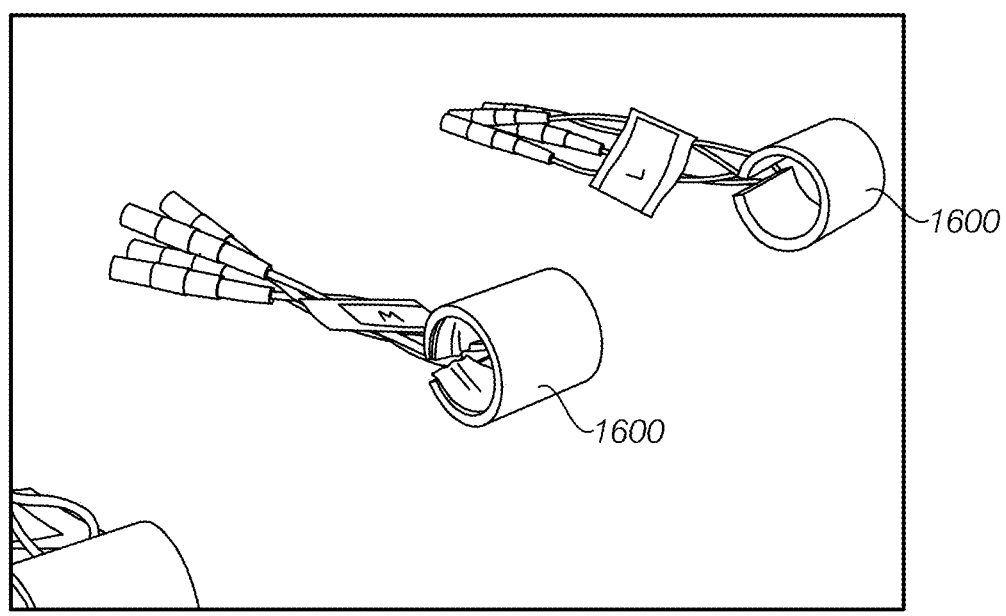
FIG. 16B illustrates embodiments of horizontal electrode configuration implemented in ring housings of different sizes. These electrode configurations were implemented and tested on three people, and paresthesia of the nerves was verified.

In another embodiment as shown in FIGS. 16A and 16B, the ring-like unit 1600 contains a horizontal electrode configuration to transcutaneously provide electrical stimulation to branches of the median, radial, and/or ulnar nerves in the finger (FIG. 16). There is an electrode pair 1602 on the dorsal side to stimulate the radial nerve, and an electrode pair 1604 on the palmar side to stimulate the median nerve. In the index figure, electrodes on the dorsal side stimulate the radial nerve, and electrodes on the palmar side stimulate the median nerve. These electrode configurations were implemented and tested on three people, and paresthesia of the nerves was verified.

Figure 17A:
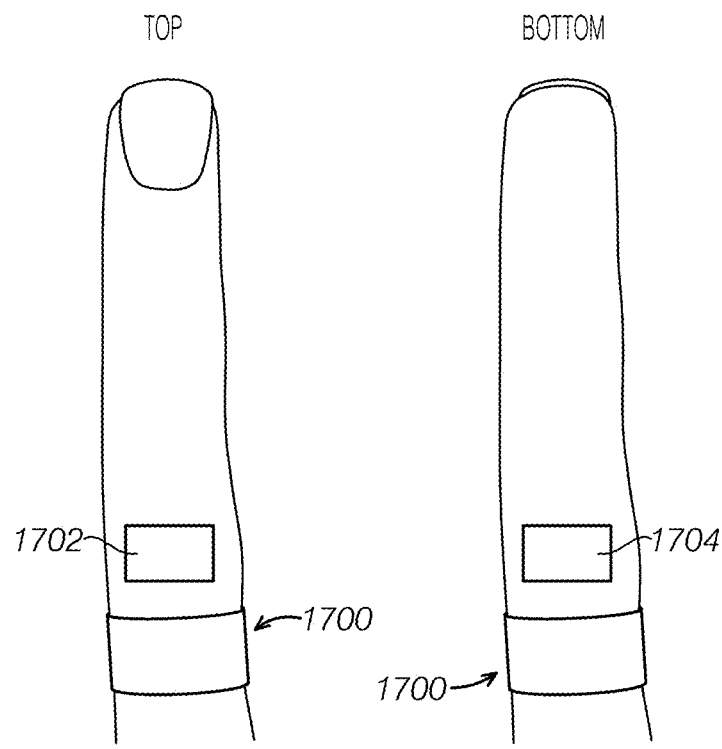
FIGS. 17A and 17B illustrate an embodiment of a horizontal electrode configuration with a single common ground electrode that wraps continuously around the finger. With the common electrode, the total electrode count is reduced to 3.
Figure 17B:
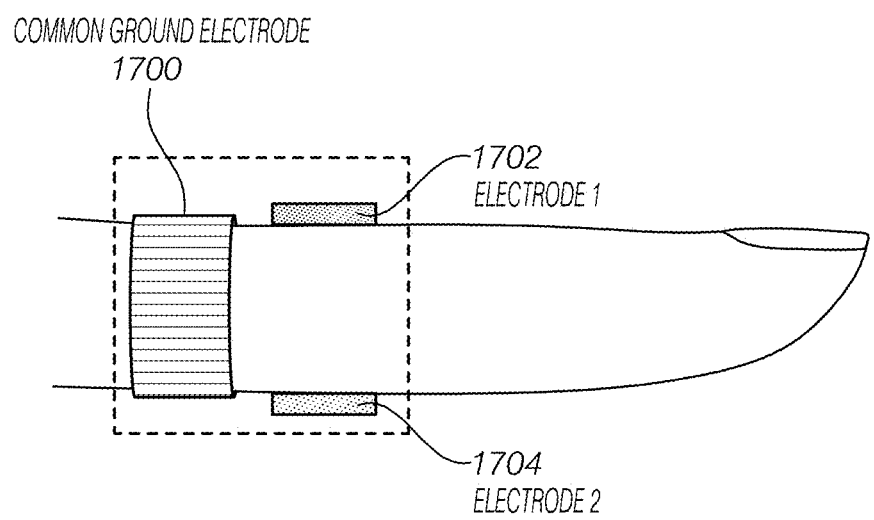
Figure 18A:
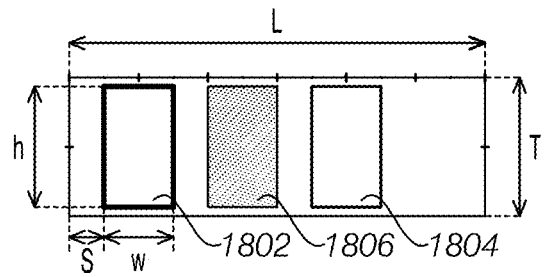
FIG. 18A-18D illustrate an embodiment of a vertical electrode configuration housed in a ring-like unit that provides electrical stimulation transcutaneously to nerves in the finger. This illustration is of an index finger with an electrode on the dorsal side to stimulate the radial nerve, and an electrode on the palmar side to stimulate the median nerve. These two electrodes share a common ground electrode that is oriented 90° between the other two electrodes. These electrode configurations were implemented and tested on three people, and paresthesia of the nerves was verified.
Figure 18A:
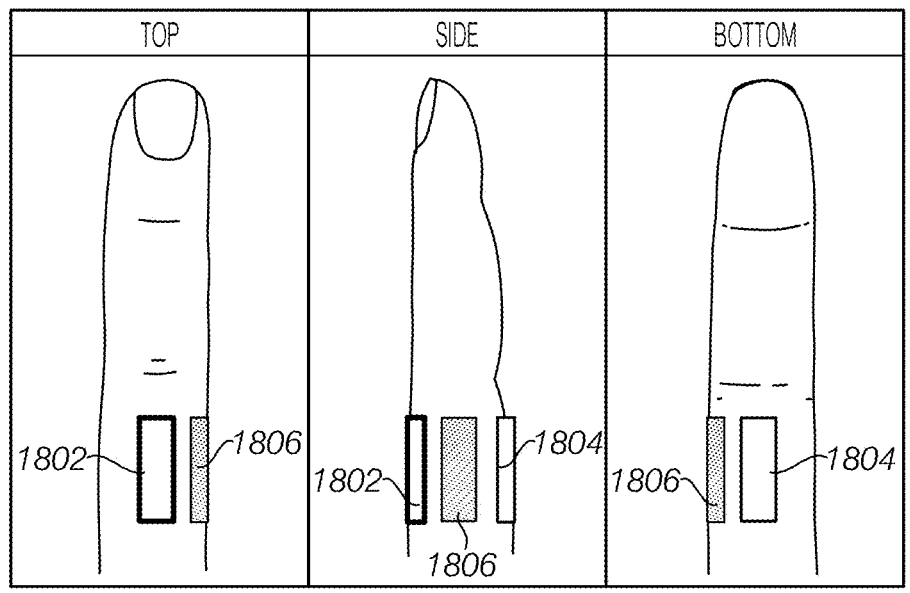
Figure 18A:
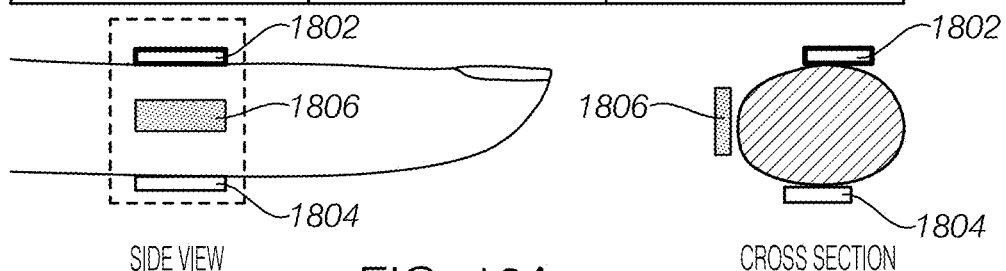
Figure 18B:
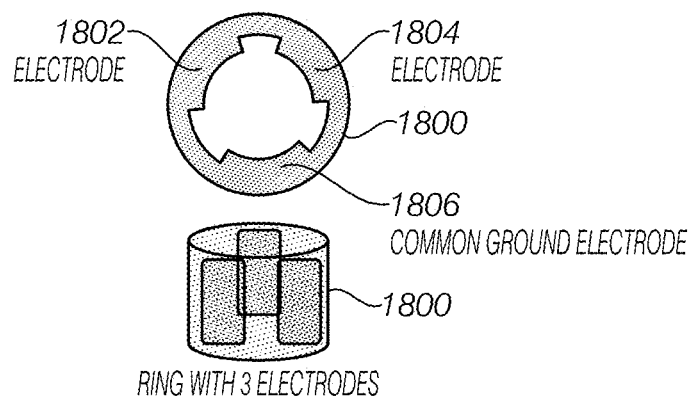
Figure 18C:
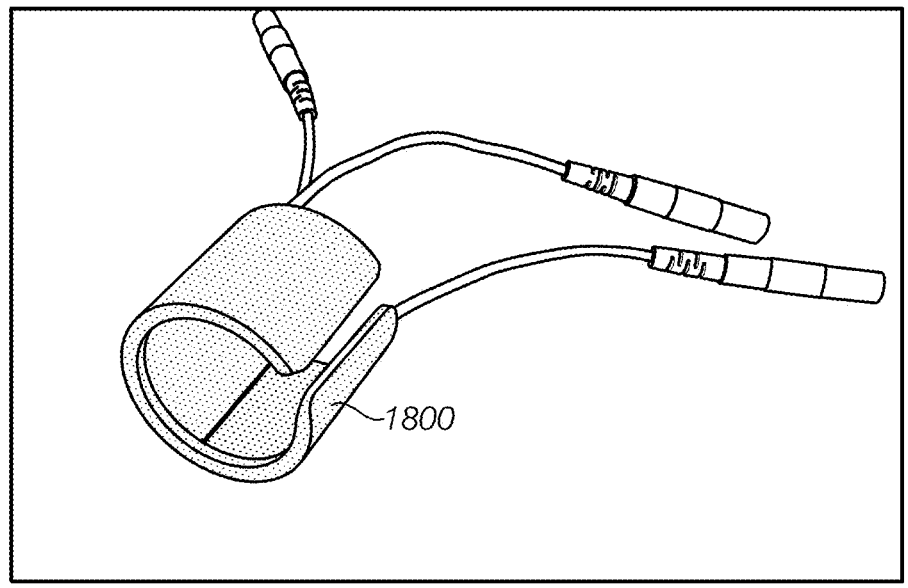
Figure 18D:
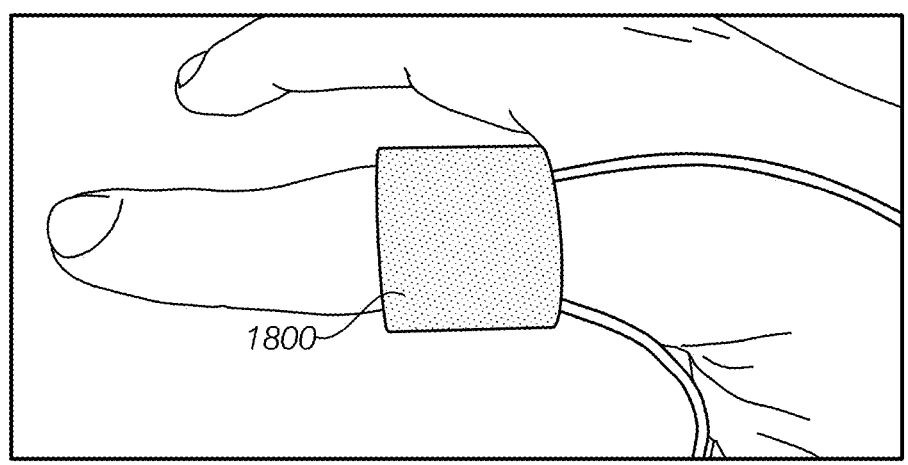

In another embodiment of the configuration above as shown in FIGS. 17A and 17B, a common electrode 1700 can be created out of two of the electrodes to reduce the total electrode count to 3 for a configuration that can stimulate a nerve on the dorsal side using a dorsal electrode 1702 and the common electrode 1700 and a nerve on the palmar side using a palmar electrode 1704 and the common electrode 1700. The common electrode can be a ring electrode that spans both sides of the finger, and as shown, the electrode pairs it forms are arranged longitudinally with respect to the finger.

In one embodiment as shown in FIGS. 18A-D, the ring-like unit 1800 contains a vertical or circumferential electrode configuration to transcutaneously provide electrical stimulation to the branches of the median, radial, and/or ulnar nerves in the finger. There is an electrode 1802 on the dorsal side to stimulate the radial nerve, and an electrode 1804 on the palmar side to stimulate the median nerve. These two electrodes share a common ground electrode 1806 that is oriented approximately 90° between the two electrodes. In the index finger, the electrode on the dorsal side stimulates the radial nerve, and the electrode on the palmar side stimulates the median nerve. These electrode configurations were implemented and tested on three people, and paresthesia of the nerves was verified.

Figure 19:
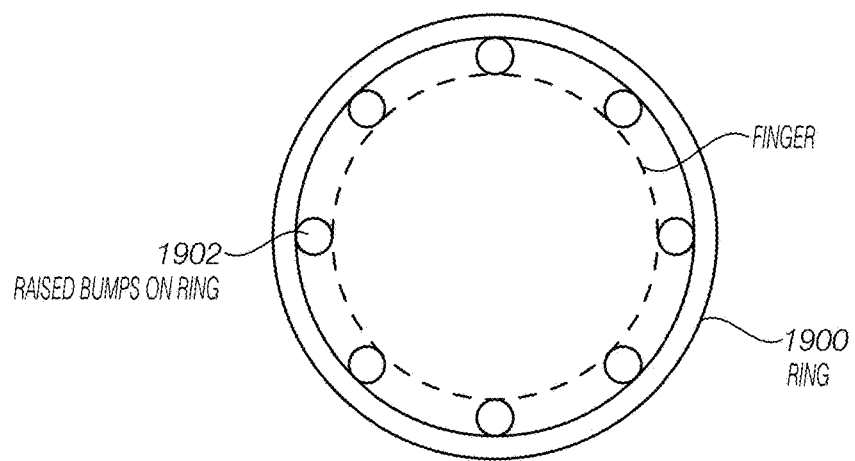
FIG. 19 illustrates an embodiment of a ring-like unit with bumps or contours on the inside surface to accommodate variation in finger size.

In one embodiment as shown in FIG. 19, the ring-like unit 1900 has bumps 1902 and contours on the inside surface of the ring. This allows better conformation to the skin to accommodate the natural variety in finger size between different people, or between different fingers on the same person. It also allows a single ring-like unit to tightly conform to a person's finger despite natural variations in finger size over time.

Figure 20:
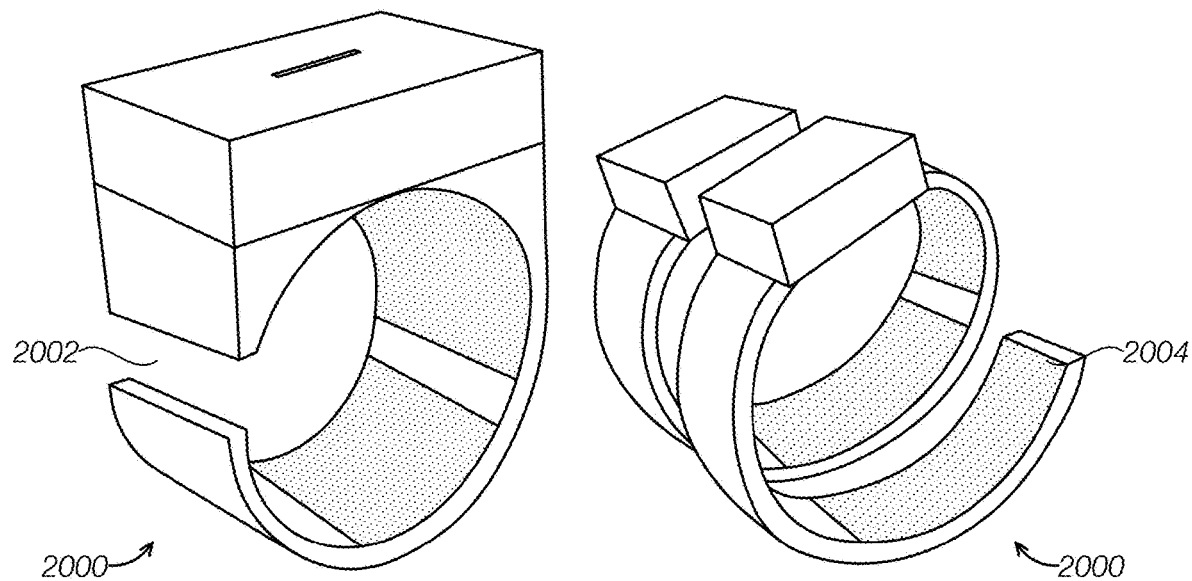
FIG. 20 illustrates an embodiment of a ring-like unit with a flexible form to accommodate variation in finger size.

In one embodiment as shown in FIG. 20, the ring-like unit 2000 may be flexible or manufactured from an elastic material, such as silicone, rubber, or elastic fabric. This allows better conformation to the skin to accommodate the natural variety in finger size between different people, or between different fingers on the same person. It also allows a single ring-like unit to tightly conform to a person's finger despite natural variations in finger size over time. The ring can have a slit 2002 or be formed from a spiral 2004 that facilitates the increase in ring diameter when needed.

Figure 21:
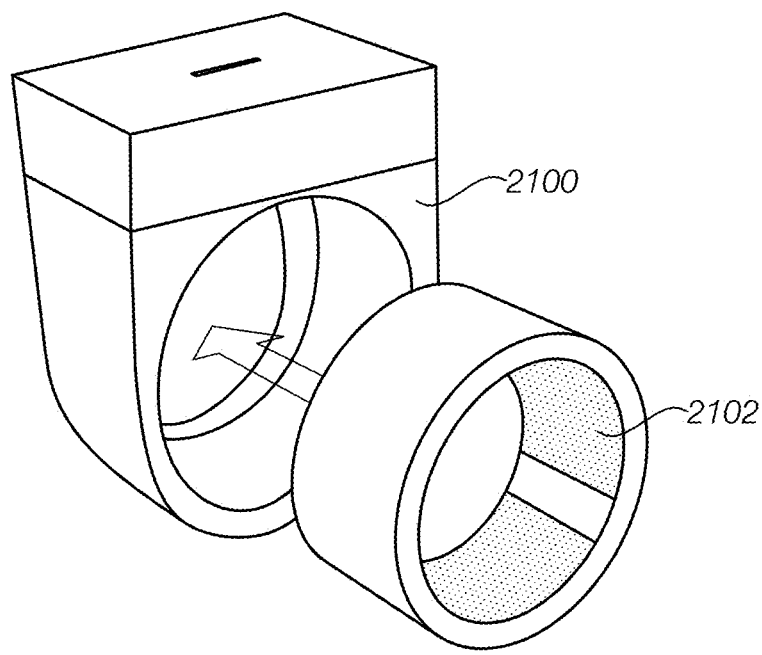
FIG. 21 illustrates an embodiment of a ring-like unit with inserts to accommodate variation in finger size.

In one embodiment as shown in FIG. 21, the ring-like unit 2100 could have separate, multiple inserts 2102 to accommodate variations in finger size. This allows better conformation to the skin to accommodate the natural variety in finger size between different people, or between different fingers on the same person. Thicker inserts can be used for people with small fingers, and thinner inserts can be used for people with large fingers. It also allows a single ring-like unit to tightly conform to a person's finger despite natural variations in finger size over time. The inserts 2102 can have electrodes and electrical contacts for electrically coupling with the ring unit.

Figure 22:
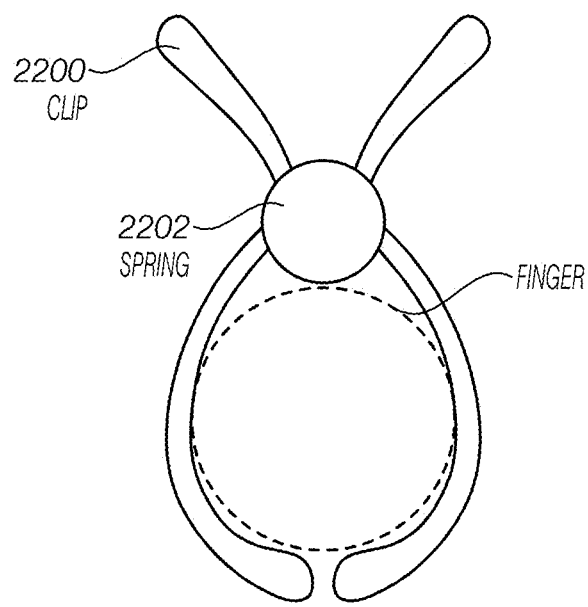
FIG. 22 illustrates an embodiment of a ring-like unit as a c-clip with a spring hinge to accommodate variation in finger size and improve ease of attaching the device to the finger.

In one embodiment as shown in FIG. 22, the ring-like unit 2200 could be in the shape of a C-clip with spring hinge 2202 that allows the device to be attached over the finger and would not require specific ring sizing. The spring-hinge would apply a small amount of pressure through the clip to ensure good conformance and contact between the electrodes and the skin. The c-clip could also be easier for people to attach to their finger, especially people with hand tremors. This allows better conformation to the skin to accommodate the natural variety in finger size between different people, or between different fingers on the same person. It also allows a single ring-like unit to tightly conform to a person's finger despite natural variations in finger size over time. Additionally, the clip could attach to the distal end of the finger (i.e., the fingertip, similar to a pulse-oximeter), as early experiments previously described show that top and middle segments can be used to successfully stimulate nerves in the finger.

Figure 23:
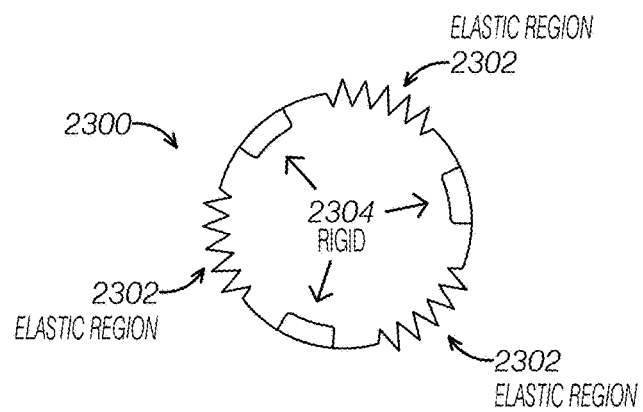
FIG. 23 illustrates an embodiment of a ring-like unit with elastic material connecting the electrodes together around the finger.

In another embodiment as shown in FIG. 23, the ring 2300 could contain neighboring regions of elastic 2302 and non-elastic 2304 materials. The nonelastic regions could contain the electrode areas while the elastic regions allow better conformance to the finger size. This is analogous to what is done in children's pants to accommodate different waist sizes.

In another embodiment, the ring-like unit connects wirelessly (e.g., low-energy Bluetooth) or is physically tethered to an external device that contains an electrical stimulation signal generator, power source, and a microprocessor to control the stimulation, such as a smart phone or tablet. The ring-like unit would transcutaneously provide electrical stimulation to the branches of the median, radial, and/or ulnar nerves in the finger.

Figure 24:
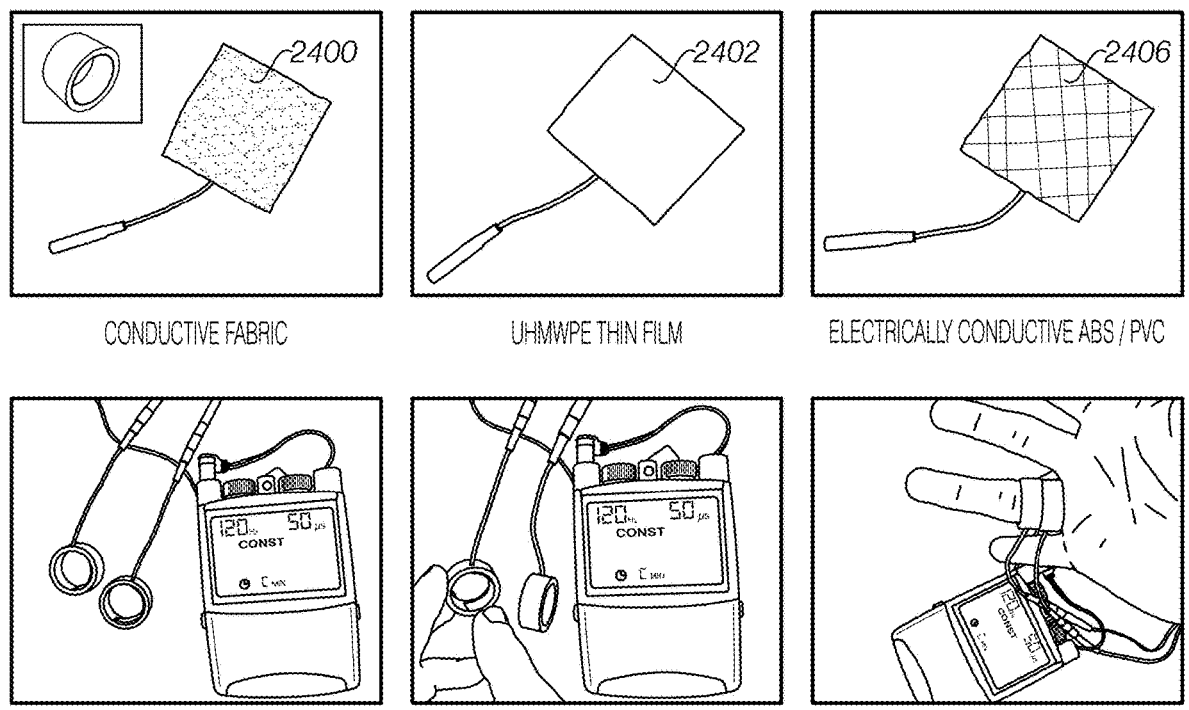
FIG. 24 illustrates various embodiments of dry-contact electrodes housed in a ring-like unit. Top panel shows three different dry electrode materials, and bottom panel shows implementation of a dry electrode ring with a thin-film ultra-high molecular weight polyethylene (UHMWPE).

In some embodiments as shown in FIG. 24, the electrodes could be dry-contact 2400 (e.g., fabric or silicone impregnated with conductive fillers such as carbon or silver particles, thin-film carbon-doped UHMWPE polymer 2402, conductive ABS/PC polymer 2404, a conductive gel (e.g., hydrogels), a wet electrode surface (e.g., a sponge with water or conductive liquids), or fine micro needles. In some embodiments, dry electrodes can be made to have better contact by attaching them to a springy/spongy surface. This produces a comfortable, conformal surface. For example, a stainless steel fabric could be sewn to a neoprene rubber. The neoprene will have enough stretch and give to allow conformance to the surface.

Figure 25:
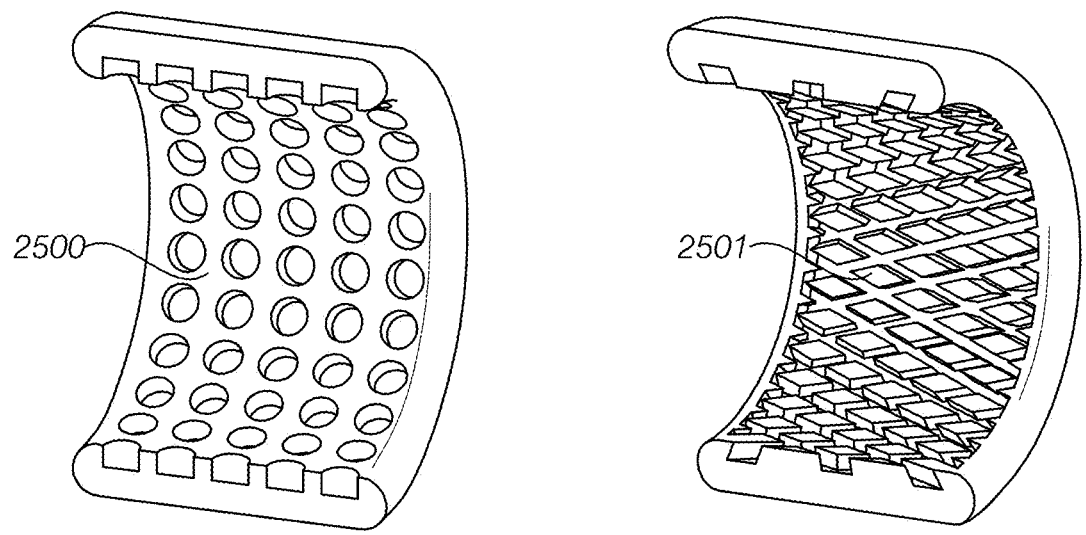
FIG. 25 illustrates a cross-sectional view of an embodiment of a ring-like unit with textured surface for capturing moisture. Moisture can improve the conductivity of the stimulation. These textured surfaces were created—when worn and run under water the units retained moisture for at least 30 minutes.

In some embodiments as shown in FIG. 25, the electrodes in a ring-like unit could have textured surfaces 2500, 2501 that trap moisture from the skin, air, or some external source, such as a sink. Moisture can improve the conductivity of the stimulation. These illustrated textured surfaces were created in ring-like units that when worn and run under water. These units retained moisture for at least 30 minutes. The ring-like unit could also have a dry contact electrode with a similar textured surface.

In some embodiments, the electrodes could be a wicking fabric impregnated with conductive fillers or fibers. The wicking fabric would draw moisture from the skin or from the surrounding air (e.g., humidity) to improve conductivity of the stimulation.

Figure 26:
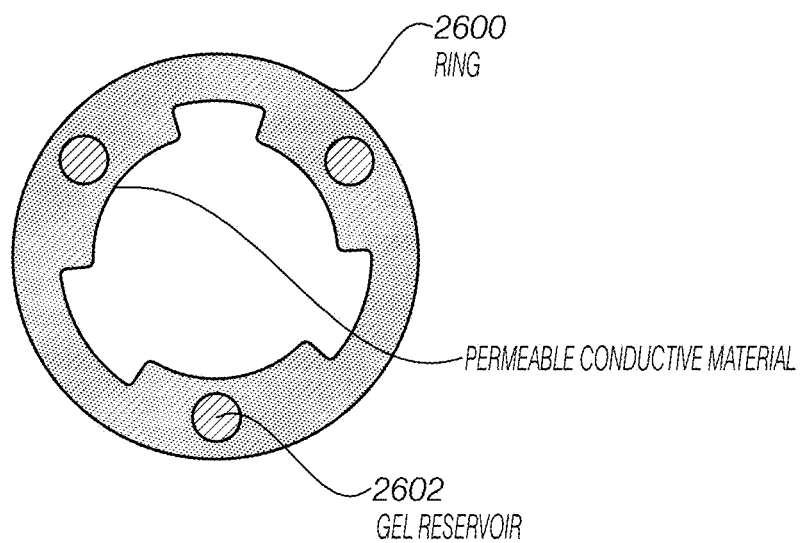
FIG. 26 illustrates an embodiment of a ring-like unit that contains a reservoir for conductive gel or liquid with a permeable membrane to slowly release the gel or liquid to the electrode-skin interface to improve stimulation conductivity.

In some embodiments as shown in FIG. 26, the ring-like unit 2600 could contain a reservoir 2602 or a plurality of reservoirs for a conductive gel or liquid that is slowly released through a permeable membrane. Fluid flow could be driven by gravity or by pressure applied to the ring manually, or from placing the ring on the finger. The reservoir could be filled by the wearer through an opening on the ring; or the reservoir could contain a wicking material that draws moisture from the skin or surrounding air.

In some embodiments, the wearable tremor monitor can use a plurality of sensors to collect, store, and analyze biological measures about the wearer including, but not limited to, motion (e.g., accelerometers, gyroscopes, magnetometer, bend sensors, barometer, altimeter), cardiovascular measures (e.g., heart rate, heart rate variability, blood pressure, cardiac output), skin conductance (e.g., skin conductance response, galvanic skin response), skin temperature, and sleep state (e.g., awake, light sleep, deep sleep, REM). In particular, studies have shown that increased stress levels can increase tremor in people with essential tremor, Parkinson's disease, and other diseases causing tremor. Thus, using statistical analysis and data mining techniques, including, but not limited to, logistic regression, linear regression, support vector machines, and Naïve Bayes classifiers, these biological measures can be analyzed to assess a person's state, including, but not limited to, stress level. This, in turn, can serve as a predictor for fluctuations in tremor level. In an early pilot study, patients were asked to perform activities prior to and after a stressful event. In this case, the stressful event was to take a timed math test. In preliminary studies, the patients' amplitude of tremor appeared to increase by about 20% after the stressful timed math test.

The wearable tremor monitor can have a microprocessor to analyze biological measures about the wearer to: determine or predict the onset of increased tremor activity, set parameters of the stimulation waveform applied by the stimulation unit, and/or adapt the stimulation waveform applied by the stimulation unit in real time. Parameters of the stimulation waveform that could be modified based on analysis of biological measures, include, but are not limited to, frequency, amplitude, shape, and burst sequence.

In one embodiment of the system, the wearable tremor monitor automatically detects and records stimulation usage to (1) track therapy compliance, (2) combine with the measurement of tremor activity to assess therapeutic effectiveness, and (3) determine or predict the onset of an increase or decrease in tremor activity.

In some embodiments, the wearable tremor monitor can have a visual, auditory, tactile (e.g., squeezing band), or vibrotactile cues to notify the wearer of key events based on analysis of biological measures, including, but not limited to, prediction of tremor onset, increase in tremor activity, and/or increase in stress level. The cuing system could also notify the wearer of other predetermined events or reminders set by the wearer. The cuing system is used to communicate information to the wearer, such as onset of increased tremor activity or other predetermined events in a more discreet, personalized way, without drawing attention from others in social situations.

In one embodiment, the wearable monitor can have a processing unit that collects, stores, processes, and analyzes the biological measures, along with other data input by the wearer.

In some embodiments, the wearable monitor can take user input about events, including diet history, medication history, caffeine intake, alcohol intake, etc. The monitor can use accelerometers to measure specific movements, gestures, or tapping patterns to record user inputs at specific prompts. Other touch sensors, such as resistive strips or pressure sensitive screens, or accelerometer and gyroscopes could be used to measure specific gestures, movements, or tapping to record user inputs. These gesture based measures to record user input minimized the complexity of steps required to input user data into the device. The data can be stored in memory and processed by the processing unit. In some embodiments, the data can be transmitted from the wearable monitor to an external computing device, such as a smartphone or a tablet.

In one embodiment, the wearable monitor can connect with other applications, such as calendars and activity logs to sync and track events, or a saved calendar can be saved and stored on the device. In some embodiments, the wearable monitor can communicate with a variety of computing devices, such as a smart phone, tablet, laptop, or desktop computer that have the appropriate software.

Figure 5B:
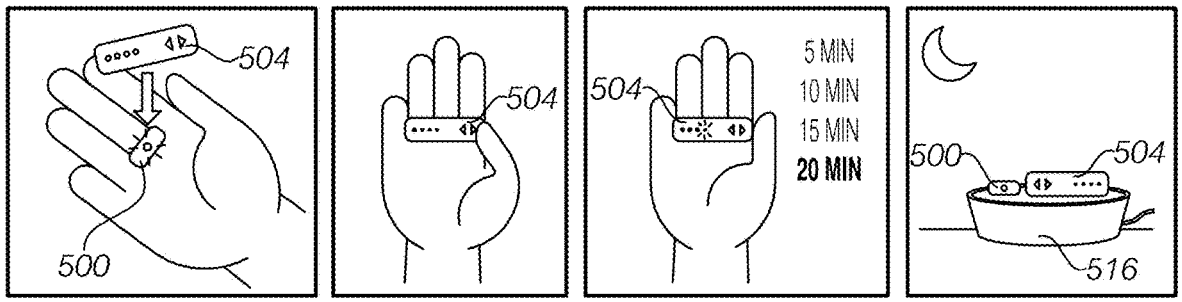
Figure 6A:
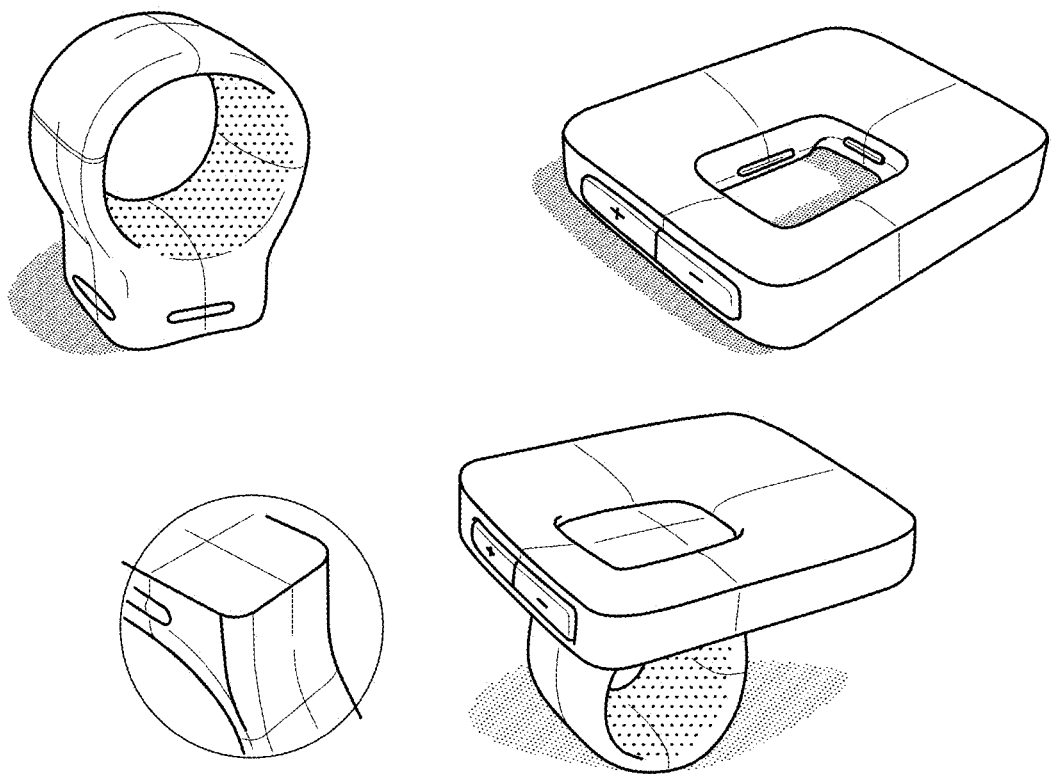
FIGS. 6A-6D illustrate various embodiments of a ring unit and a stimulation unit.
Figure 6B:
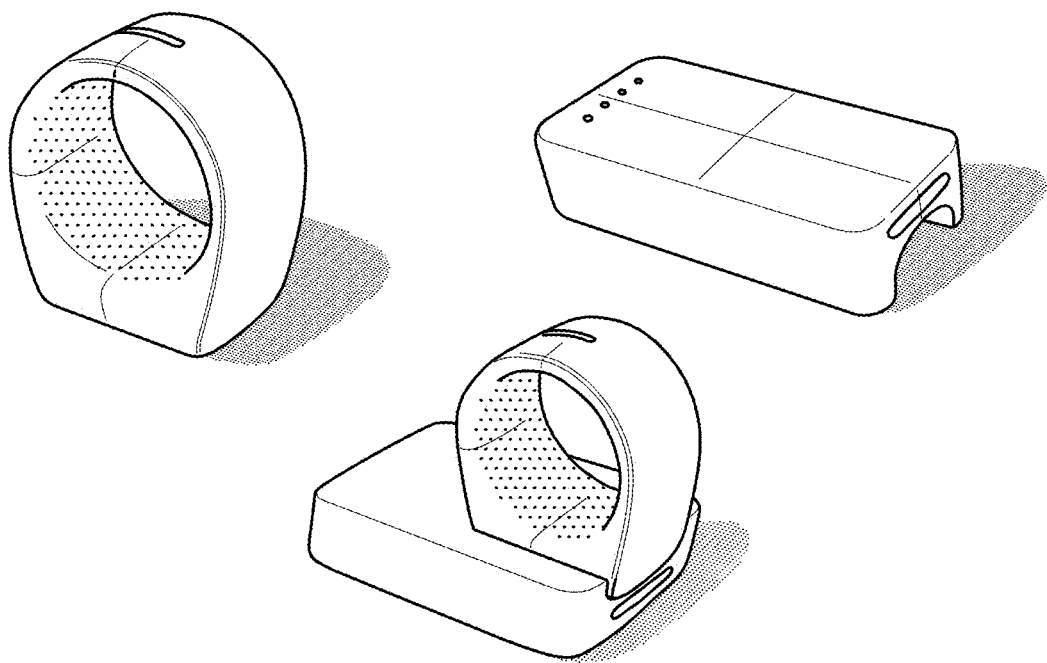
Figure 6C:
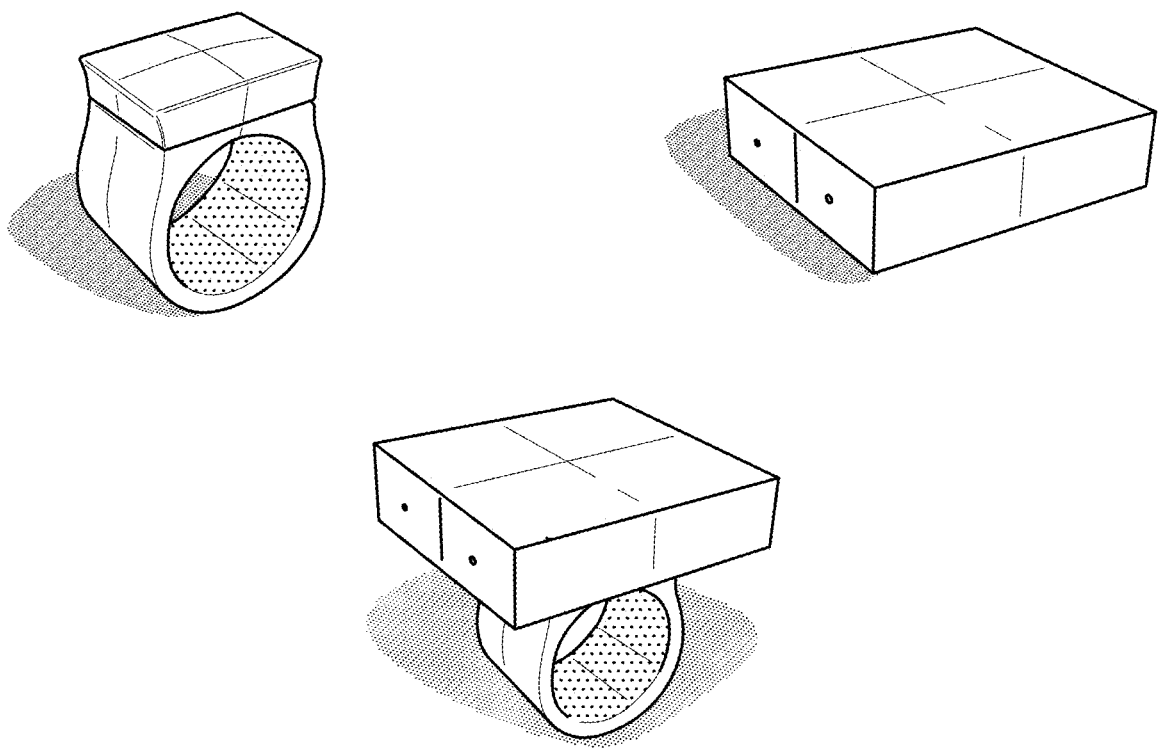
Figure 6D:
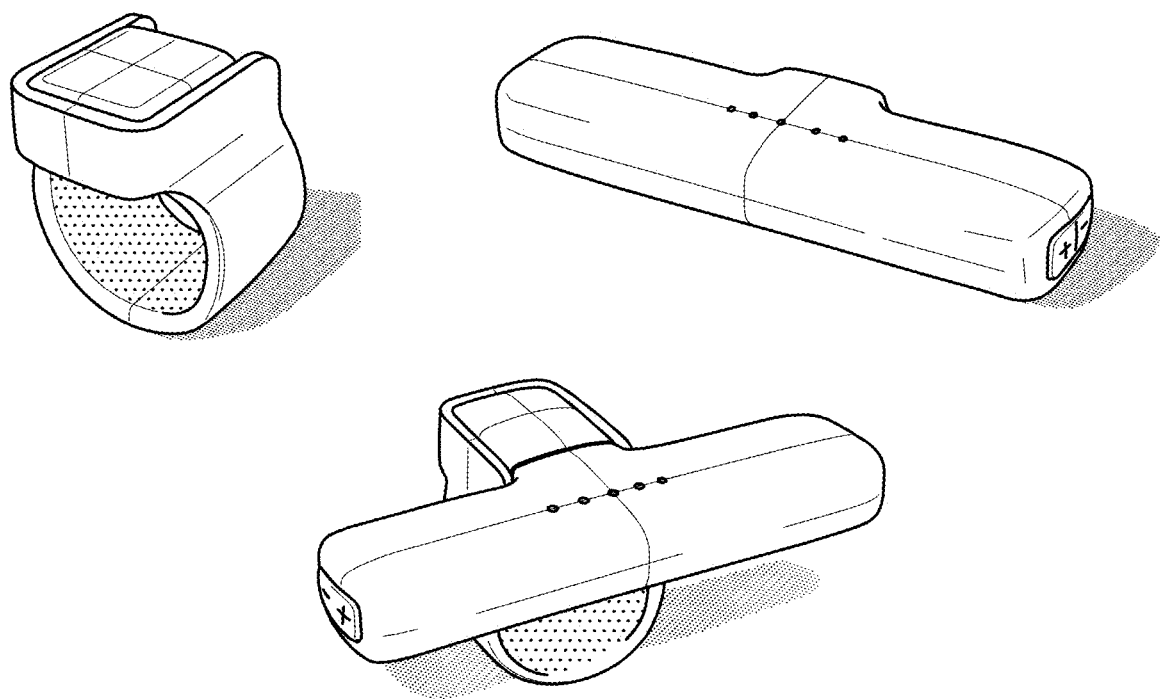

In one embodiment, the wearable monitor can have a GPS or similar device to track the location and assess activity of the wearer. GPS measures can be combined with mapping or location systems to determine context of the wearer's activity (e.g., gym versus office) or determine changes in elevation during specific activities, such as running or cycling. This may also be done by adding sensors to the wearable monitor such as barometers and altimeters In one embodiment, the ring and stimulation unit have a unique power charging station that can simultaneously charge both devices units. The charging station could have a custom direct electrical connection to the power source of the stimulation units or could charge the units inductively (e.g., wirelessly) in a close proximity (FIG. 5).

In one embodiment, the wearable monitor can track parameters about stimulation provided by the stimulation unit, including time of stimulation, duration of the stimulation session, and power used by the stimulation unit. This data can be stored on memory in the wearable monitor, processed by the wearable monitor, and/or transmitted to an external computing device, such as a smartphone, tablet, laptop, or desktop computer.

In some embodiments, the wearable monitor can communicate with an external computer or device (e.g., tablet, smartphone, smartwatch, or custom base station) to store data. Communication between the monitor and external device can be a direct, physical connection, or with a wireless communication connection such as Bluetooth, GSM, or cellular.

In some embodiments, the power source can be a rechargeable battery, which can be housed in the ring or stimulation unit, or can be used as a detachable power source that can be inserted into a port or receptacle in the ring or stimulation unit. Recharging the rechargeable battery can done through a wired connection or wirelessly.

In other embodiments, the power source can be a capacitor or a supercapacitor. Use of a capacitor may allow the size of the power source to be substantially reduced, which is important for a device that is designed to be worn on the finger. The capacitor can be recharged by an external power source through a wired connection or wirelessly (e.g., inductively). Recharging the capacitor can be performed between stimulations, during stimulations, or both.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present.

In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wearable ring device for treating hand tremors by electrically stimulating one or more sensory nerves on a finger of a patient's hand, the device comprising:
    an annular member defining an aperture that is sized to receive a finger of the patient;
    a first electrode, a second electrode, and a third electrode housed on an inside surface of the annular member and configured to be in contact with the patient's skin when worn on the finger; and
    a stimulation unit that is configured to connect to the annular member, wherein when the unit is connected to the annular member the unit is in electrical communication to the first electrode, the second electrode, and the third electrode, wherein the unit houses a power source and a pulse generator configured to deliver pulsed electrical stimulation to the one or more sensory nerves in the finger,
    wherein when worn the first electrode is configured to be positioned on the dorsal side of the first finger, the second electrode is configured to be positioned on the palmar side of the first finger, and the third electrode is a circumferential electrode configured to be positioned circumferentially on the inside surface of the annular member and proximal of first and second electrodes.

2. The device of claim 1, wherein the third electrode is a common ground electrode.

3. The device of claim 2, wherein the finger is the index finger, middle finger, or the ring finger.

4. The device of claim 1, further comprising a fourth electrode housed on the inside surface of the annular member.

5. The device of claim 1, wherein the first, second, and third electrodes comprise a dry conductive polymer or rubber with a textured surface configured to capture moisture from the skin, air, or other external sources,
    wherein the first, second, and third electrodes comprise a wicking conductive fabric configured to capture moisture from the skin, air, or other external sources,
    wherein the device further comprises a wireless transceiver electrically connected to the pulse generator and configured to communicate with at least one external electronic device,
    wherein the annular member comprises a flexible housing material, and the first, second, and third electrodes are electrically connected with flexible electronic circuitry that is configured to conform to a predetermined range of finger diameters and configured to accommodate variation in finger diameter over time,
    wherein the annular member comprises one or more motion sensors, and wherein the pulse generator is configured to modulate the pulsed electrical stimulation based on measurements of tremor motion and activity from the one or more motion sensors, wherein the one or more motion sensors are selected from the group consisting of an inertial measurement unit, an accelerometer, a gyroscope, and a magnetometer,
    wherein the one or more motion sensors in the annular member along with a processor located in the stimulation unit or at least one external device are configured to measure and detect one or more predetermined motions and to modulate the pulsed electrical stimulation based on the measurement and detection of the one or more predetermined motions.

6. A wearable ring device for electrically stimulating one or more sensory nerves on a finger of a patient's hand, the device comprising:
    an annular member defining an aperture that is sized to receive a finger of the patient;
    a first electrode, a second electrode, and a third electrode housed on an inside surface of the annular member and configured to be in contact with the patient's skin when worn on the finger; and
    a stimulation unit that is configured to connect to the annular member, wherein when the unit is connected to the annular member the unit is in electrical communication to the first electrode, the second electrode, and the third electrode, wherein the unit houses a power source and a pulse generator configured to deliver pulsed electrical stimulation to the one or more sensory nerves in the finger,
    wherein when worn the first electrode is configured to be positioned on the dorsal side of the first finger, the second electrode is configured to be positioned on the palmar side of the first finger, and the third electrode is a circumferential electrode configured to be positioned circumferentially on the inside surface of the annular member and proximal of first and second electrodes.

7. The device of claim 6, wherein the third electrode is a common ground electrode.

8. The device of claim 6, wherein the finger is the index finger, middle finger, or the ring finger.

9. The device of claim 6, further comprising a fourth electrode housed on the inside surface of the annular member.

10. The device of claim 6, wherein the power source is a capacitor.

11. The device of claim 6, wherein the power source is a rechargeable battery.

12. The device of claim 6, wherein the stimulation unit is detachable.

13. The device of claim 6, wherein the third electrode is configured to be positioned approximately equidistant between the first and second electrodes when the device is worn.

14. The device of claim 6, wherein the first, second, and third electrodes comprise a dry conductive polymer or rubber with a textured surface configured to capture moisture from the skin, air, or other external sources.

15. The device of claim 6, wherein the first, second, and third electrodes comprise a wicking conductive fabric configured to capture moisture from the skin, air, or other external sources.

16. The device of claim 6, wherein the first, second, and third electrodes comprise a dry conductive polymer or rubber with a textured surface configured to capture moisture from the skin, air, or other external sources,
    wherein the first, second, and third electrodes comprise a wicking conductive fabric configured to capture moisture from the skin, air, or other external sources,
    wherein the device further comprises a wireless transceiver electrically connected to the pulse generator and configured to communicate with at least one external electronic device,
    wherein the annular member comprises a flexible housing material, and the first, second, and third electrodes are electrically connected with flexible electronic circuitry that is configured to conform to a predetermined range of finger diameters and configured to accommodate variation in finger diameter over time,
    wherein the annular member comprises one or more motion sensors, and wherein the pulse generator is configured to modulate the pulsed electrical stimulation based on measurements of tremor motion and activity from the one or more motion sensors, wherein the one or more motion sensors are selected from the group consisting of an inertial measurement unit, an accelerometer, a gyroscope, and a magnetometer, wherein the one or more motion sensors in the annular member along with a processor located in the stimulation unit or at least one external device are configured to measure and detect one or more predetermined motions and to modulate the pulsed electrical stimulation based on the measurement and detection of the one or more predetermined motions.

17. A method of electrically stimulating one or more sensory nerves on a finger of a patient's hand, the method comprising:

providing a wearable stimulator comprising:

an annular member defining an aperture that is sized to receive a finger of the patient;

a first electrode, a second electrode, and a third electrode housed on an inside surface of the annular member and configured to be in contact with the patient's skin when worn on the finger; and a stimulation unit that is configured to connect to the annular member, wherein when the unit is connected to the annular member the unit is in electrical communication to the first electrode, the second electrode, and the third electrode, wherein the unit houses a power source and a pulse generator configured to deliver pulsed electrical stimulation to the one or more sensory nerves in the finger, wherein when worn the first electrode is configured to be positioned on the dorsal side of the first finger, the second electrode is configured to be positioned on the palmar side of the first finger, and the third electrode is a circumferential electrode configured to be positioned circumferentially on the inside surface of the annular member and proximal of first and second electrodes; and stimulating the one or more sensory nerves in a first finger of the patient according to a set of stimulation parameters using the wearable stimulator, wherein the one or more sensory nerves is selected from the group consisting of the medial nerve, the radial nerve, and the ulnar nerve.

18. The method of claim 17, wherein stimulating one or more sensory nerves comprises stimulating two sensory nerves.

19. The method of claim 17, for treating tremor of the patient's hand, wherein the method further comprises:

measuring motion in the patient's hand with a sensor worn on one of the patient's fingers; and determining one or more characteristics of the tremor based on a signal generated by the motion sensor, wherein the one or more characteristics of the tremor is selected from the group consisting of the tremor frequency, tremor amplitude, and tremor phase.

20. The method of claim 17, wherein the set of stimulation parameters is based in part on the one or more of the determined tremor characteristics.

* * * * *